(12) United States Patent
Burpee et al.

(10) Patent No.: US 9,592,137 B2
(45) Date of Patent: Mar. 14, 2017

(54) FLEXIBLE STENT

(71) Applicant: Flexible Stenting Solutions, Inc., Eatontown, NJ (US)

(72) Inventors: Janet Burpee, Fair Haven, NJ (US); Bradley Beach, Belmar, NJ (US)

(73) Assignee: FLEXIBLE STENTING SOLUTIONS, INC., Eatontown, NJ (US)

( * ) Notice: Subject to any disclaimer, the term of this patent is extended or adjusted under 35 U.S.C. 154(b) by 248 days.

(21) Appl. No.: 14/303,766

(22) Filed: Jun. 13, 2014

(65) Prior Publication Data
US 2014/0379066 A1 Dec. 25, 2014

Related U.S. Application Data

(62) Division of application No. 12/884,514, filed on Sep. 17, 2010, now abandoned, which is a division of
(Continued)

(51) Int. Cl.
*A61F 2/915* (2013.01)
*A61F 2/88* (2006.01)
(Continued)

(52) U.S. Cl.
CPC ............... *A61F 2/88* (2013.01); *A61F 2/07* (2013.01); *A61F 2/91* (2013.01); *A61F 2/915* (2013.01);
(Continued)

(58) Field of Classification Search
CPC ...... A61F 2/04; A61F 2/06; A61F 2/82; A61F 2/86; A61F 2/88; A61F 2/885; A61F 2/89;
(Continued)

(56) References Cited

U.S. PATENT DOCUMENTS

| | | |
|---|---|---|
| 4,425,908 A | 1/1984 | Simon |
| 4,665,906 A | 5/1987 | Jervis |

(Continued)

FOREIGN PATENT DOCUMENTS

| | | |
|---|---|---|
| CN | 1186423 | 7/1998 |
| EP | 0870483 A2 | 10/1998 |

(Continued)

OTHER PUBLICATIONS

New Zealand Office Action, dated May 7, 2013, for New Zealand Patent Appln. No. 609963.
(Continued)

*Primary Examiner* — Ryan J Severson
(74) *Attorney, Agent, or Firm* — Khoi Q. Ta

(57) ABSTRACT

A flexible stent structure includes a plurality of axially spaced strut portions defining generally tubular axial segments of the stent and constructed to be radially expandable. A helical portion is interposed axially between two strut portions and has a plurality of helical elements connected between circumferentially spaced locations on the two strut portions. The helical elements extend helically between those locations and the length of a helical element is sufficient so that, when the stent is in a radially expanded state, it can simultaneously withstand repeated axial compression or expansion and bending.

5 Claims, 15 Drawing Sheets

Related U.S. Application Data application No. 11/397,987, filed on Apr. 4, 2006, now Pat. No. 7,803,180.

(51) Int. Cl.

| | | |
|---|---|---|
| *A61F 2/91* | (2013.01) | |
| *A61F 2/07* | (2013.01) | |
| *A61F 2/966* | (2013.01) | |

(52) U.S. Cl.
CPC .... *A61F 2/966* (2013.01); *A61F 2002/91525* (2013.01); *A61F 2002/91533* (2013.01); *A61F 2002/91558* (2013.01); *A61F 2230/0054* (2013.01)

(58) Field of Classification Search
CPC .... A61F 2/90; A61F 2/91; A61F 2/915; A61F 2002/825; A61F 2002/828; A61F 2002/91508; A61F 2002/91516; A61F 2002/91525; A61F 2002/91533; A61F 2002/91541; A61F 2002/9155; A61F 2002/91558
See application file for complete search history.

(56) References Cited

U.S. PATENT DOCUMENTS

| | | | |
|---|---|---|---|
| 4,813,925 A | | 3/1989 | Anderson, Jr. et al. |
| 5,102,417 A | * | 4/1992 | Palmaz ............... A61F 2/91 604/103.05 |
| 5,104,404 A | | 4/1992 | Wolff |
| 5,133,732 A | | 7/1992 | Wiktor |
| 5,190,546 A | | 3/1993 | Jervis |
| 5,197,978 A | | 3/1993 | Hess et al. |
| 5,266,073 A | | 11/1993 | Wall |
| 5,275,622 A | | 1/1994 | Lazarus et al. |
| 5,292,321 A | | 3/1994 | Lee |
| 5,383,892 A | | 1/1995 | Cardon et al. |
| 5,395,390 A | | 3/1995 | Simon et al. |
| 5,449,373 A | * | 9/1995 | Pinchasik ............ A61F 2/856 606/198 |
| 5,507,767 A | | 4/1996 | Maeda et al. |
| 5,545,210 A | * | 8/1996 | Hess ............... A61F 2/86 128/898 |
| 5,591,197 A | | 1/1997 | Orth et al. |
| 5,591,226 A | | 1/1997 | Trerotola et al. |
| 5,597,378 A | | 1/1997 | Jervis |
| 5,649,949 A | | 7/1997 | Wallace et al. |
| 5,662,703 A | | 9/1997 | Yurek et al. |
| 5,669,932 A | * | 9/1997 | Fischell ............ A61F 2/91 606/198 |
| 5,693,085 A | | 12/1997 | Buirge et al. |
| 5,697,971 A | | 12/1997 | Fischell et al. |
| 5,716,396 A | | 2/1998 | Williams, Jr. |
| 5,718,713 A | | 2/1998 | Frantzen |
| 5,741,327 A | | 4/1998 | Frantzen |
| 5,749,919 A | * | 5/1998 | Blanc ............... A61F 2/88 606/194 |
| 5,755,781 A | * | 5/1998 | Jayaraman ........... A61F 2/91 623/1.16 |
| 5,776,142 A | | 7/1998 | Gunderson |
| 5,782,838 A | | 7/1998 | Beyar et al. |
| 5,800,456 A | | 9/1998 | Maeda et al. |
| 5,807,404 A | * | 9/1998 | Richter ............. A61F 2/91 623/1.16 |
| 5,810,872 A | * | 9/1998 | Kanesaka ............ A61F 2/91 606/198 |
| 5,824,041 A | | 10/1998 | Lenker et al. |
| 5,824,059 A | * | 10/1998 | Wijay ............... A61F 2/90 623/1.15 |
| 5,833,699 A | | 11/1998 | Chuter |
| 5,836,964 A | | 11/1998 | Richter et al. |
| 5,843,120 A | | 12/1998 | Israel et al. |
| 5,843,175 A | | 12/1998 | Frantzen |
| 5,876,432 A | | 3/1999 | Lau et al. |
| 5,876,434 A | | 3/1999 | Flomenblit et al. |
| 5,891,192 A | | 4/1999 | Murayama et al. |
| 5,907,893 A | | 6/1999 | Zadno-Azizi et al. |
| 5,911,754 A | * | 6/1999 | Kanesaka ............ A61F 2/91 606/198 |
| 5,913,895 A | | 6/1999 | Burpee et al. |
| 5,913,896 A | | 6/1999 | Boyle et al. |
| 5,913,897 A | | 6/1999 | Corso, Jr. et al. |
| 5,925,061 A | | 7/1999 | Ogi et al. |
| 5,954,743 A | | 9/1999 | Jang |
| 5,968,088 A | | 10/1999 | Hansen et al. |
| 5,976,153 A | | 11/1999 | Fischell et al. |
| 5,980,552 A | * | 11/1999 | Pinchasik ............ A61F 2/856 623/1.16 |
| 5,989,280 A | | 11/1999 | Euteneuer et al. |
| 6,013,854 A | | 1/2000 | Moriuchi |
| 6,017,365 A | | 1/2000 | Von Oepen |
| 6,022,374 A | | 2/2000 | Imran |
| 6,033,433 A | * | 3/2000 | Ehr ............... A61F 2/91 623/1.16 |
| 6,039,756 A | * | 3/2000 | Jang ............... A61F 2/91 623/1.15 |
| 6,042,597 A | | 3/2000 | Kveen et al. |
| 6,051,021 A | | 4/2000 | Frid |
| 6,059,808 A | | 5/2000 | Boussignac et al. |
| 6,059,813 A | | 5/2000 | Vrba et al. |
| 6,117,165 A | | 9/2000 | Becker |
| 6,142,987 A | | 11/2000 | Tsugita |
| 6,146,417 A | * | 11/2000 | Ischinger ........... A61F 2/90 623/1.1 |
| 6,152,957 A | * | 11/2000 | Jang ............... A61F 2/91 623/1.1 |
| 6,156,062 A | | 12/2000 | McGuinness |
| 6,165,210 A | | 12/2000 | Lau et al. |
| 6,168,621 B1 | | 1/2001 | Vrba |
| 6,190,406 B1 | | 2/2001 | Duerig et al. |
| 6,221,081 B1 | | 4/2001 | Mikus et al. |
| 6,231,598 B1 | * | 5/2001 | Berry ............... A61L 31/022 623/1.15 |
| 6,238,409 B1 | | 5/2001 | Hojeibane |
| 6,241,757 B1 | | 6/2001 | An et al. |
| 6,241,762 B1 | * | 6/2001 | Shanley ............ A61F 2/91 623/1.17 |
| 6,245,101 B1 | * | 6/2001 | Drasler ............. A61F 2/91 623/1.15 |
| 6,254,609 B1 | | 7/2001 | Vrba et al. |
| 6,261,319 B1 | * | 7/2001 | Kveen ............... A61F 2/91 623/1.15 |
| 6,264,690 B1 | | 7/2001 | Von Oepen |
| 6,287,333 B1 | | 9/2001 | Appling et al. |
| 6,293,966 B1 | | 9/2001 | Frantzen |
| 6,302,907 B1 | * | 10/2001 | Hijlkema ............ A61F 2/89 623/1.15 |
| 6,306,141 B1 | | 10/2001 | Jervis |
| 6,334,871 B1 | | 1/2002 | Dor et al. |
| 6,340,367 B1 | | 1/2002 | Stinson et al. |
| 6,342,066 B1 | | 1/2002 | Toro et al. |
| 6,348,065 B1 | | 2/2002 | Brown et al. |
| 6,352,552 B1 | * | 3/2002 | Levinson ........... A61F 2/91 623/1.15 |
| 6,355,059 B1 | | 3/2002 | Richter et al. |
| 6,369,355 B1 | | 4/2002 | Saunders |
| 6,402,777 B1 | | 6/2002 | Globerman et al. |
| 6,416,543 B1 | | 7/2002 | Hilaire et al. |
| 6,423,091 B1 | * | 7/2002 | Hojeibane .......... A61F 2/88 623/1.15 |
| 6,432,132 B1 | | 8/2002 | Cottone et al. |
| 6,464,720 B2 | | 10/2002 | Boatman et al. |
| 6,475,237 B2 | * | 11/2002 | Drasler ............. A61F 2/91 623/1.15 |
| 6,478,816 B1 | * | 11/2002 | Kveen ............... A61F 2/91 623/1.15 |
| 6,485,507 B1 | | 11/2002 | Walak et al. |
| 6,488,703 B1 | * | 12/2002 | Kveen ............... A61F 2/91 623/1.15 |
| 6,492,615 B1 | | 12/2002 | Flanagan |
| 6,503,270 B1 | | 1/2003 | Richter et al. |

(56) References Cited

U.S. PATENT DOCUMENTS

| | | | |
|---|---|---|---|
| 6,506,211 B1 | 1/2003 | Skubitz et al. | |
| 6,517,567 B2 | 2/2003 | Bass et al. | |
| 6,517,569 B2 | 2/2003 | Mikus et al. | |
| 6,533,807 B2 | 3/2003 | Wolinsky et al. | |
| 6,544,278 B1 | 4/2003 | Vrba et al. | |
| 6,551,351 B2 * | 4/2003 | Smith | A61F 2/91 623/1.15 |
| 6,562,067 B2 | 5/2003 | Mathis | |
| 6,565,595 B1 | 5/2003 | DiCaprio et al. | |
| 6,579,308 B1 | 6/2003 | Jansen et al. | |
| 6,585,758 B1 * | 7/2003 | Chouinard | A61F 2/91 623/1.16 |
| 6,599,314 B2 | 7/2003 | Mathis | |
| 6,602,281 B1 * | 8/2003 | Klein | A61F 2/86 623/1.15 |
| 6,605,111 B2 | 8/2003 | Bose et al. | |
| 6,607,552 B1 | 8/2003 | Hanson | |
| 6,612,012 B2 | 9/2003 | Mitelberg et al. | |
| 6,613,077 B2 | 9/2003 | Gilligan et al. | |
| 6,616,666 B1 | 9/2003 | Michelson | |
| 6,632,236 B2 * | 10/2003 | Hogendijk | A61B 17/22031 606/198 |
| 6,656,219 B1 | 12/2003 | Wiktor | |
| 6,663,664 B1 | 12/2003 | Pacetti | |
| 6,669,721 B1 | 12/2003 | Bose et al. | |
| 6,676,683 B1 | 1/2004 | Addis | |
| 6,676,696 B1 | 1/2004 | Marotta et al. | |
| 6,679,911 B2 * | 1/2004 | Burgermeister | A61F 2/91 623/1.15 |
| 6,706,062 B2 | 3/2004 | Vardi et al. | |
| 6,730,117 B1 | 5/2004 | Tseng et al. | |
| 6,736,839 B2 | 5/2004 | Cummings | |
| 6,736,844 B1 | 5/2004 | Glatt et al. | |
| 6,740,113 B2 | 5/2004 | Vrba | |
| 6,743,252 B1 * | 6/2004 | Bates | A61F 2/91 623/1.15 |
| 6,746,475 B1 | 6/2004 | Rivelli, Jr. | |
| 6,746,479 B2 | 6/2004 | Ehr et al. | |
| 6,761,731 B2 | 7/2004 | Majercak | |
| 6,764,506 B2 | 7/2004 | Roubin et al. | |
| 6,805,898 B1 | 10/2004 | Wu et al. | |
| 6,821,292 B2 | 11/2004 | Pazienza et al. | |
| 6,830,638 B2 | 12/2004 | Boylan et al. | |
| 6,833,002 B2 | 12/2004 | Stack et al. | |
| 6,843,802 B1 | 1/2005 | Villalobos et al. | |
| 6,852,124 B2 | 2/2005 | Cox et al. | |
| 6,860,899 B1 | 3/2005 | Rivelli, Jr. | |
| 6,867,389 B2 | 3/2005 | Shapovalov et al. | |
| 6,878,162 B2 * | 4/2005 | Bales | A61F 2/88 623/1.15 |
| 6,896,696 B2 * | 5/2005 | Doran | A61F 2/91 623/1.15 |
| 6,899,727 B2 | 5/2005 | Armstrong et al. | |
| 6,899,730 B1 | 5/2005 | Rivelli, Jr. | |
| 6,916,617 B2 | 7/2005 | Gonsalves et al. | |
| 6,918,928 B2 | 7/2005 | Wolinsky et al. | |
| 6,923,828 B1 | 8/2005 | Wiktor | |
| 6,923,829 B2 | 8/2005 | Boyle et al. | |
| 6,942,682 B2 | 9/2005 | Vrba et al. | |
| 6,945,993 B2 * | 9/2005 | Kveen | A61F 2/91 623/1.15 |
| 6,949,120 B2 * | 9/2005 | Kveen | A61F 2/91 623/1.15 |
| 6,955,685 B2 | 10/2005 | Escamilla et al. | |
| 6,962,604 B2 | 11/2005 | Hijlkema | |
| 6,969,401 B1 | 11/2005 | Marotta et al. | |
| 6,969,402 B2 * | 11/2005 | Bales | A61F 2/91 623/1.15 |
| 6,981,985 B2 | 1/2006 | Brown et al. | |
| 6,997,947 B2 | 2/2006 | Walak et al. | |
| 7,004,960 B2 | 2/2006 | Daoud | |
| 7,004,968 B2 * | 2/2006 | Lootz | A61F 2/91 623/1.15 |
| 7,018,403 B1 | 3/2006 | Pienknagura | |
| 7,033,386 B2 | 4/2006 | Richter et al. | |
| 7,044,965 B1 | 5/2006 | Spielberg | |
| 7,052,511 B2 | 5/2006 | Weldon et al. | |
| 7,081,132 B2 | 7/2006 | Cook et al. | |
| 7,105,199 B2 | 9/2006 | Blinn et al. | |
| 7,108,677 B2 | 9/2006 | Courtney et al. | |
| 7,108,716 B2 | 9/2006 | Burnside et al. | |
| 7,122,048 B2 | 10/2006 | DiMatteo et al. | |
| 7,128,756 B2 | 10/2006 | Lowe et al. | |
| 7,131,993 B2 * | 11/2006 | Gregorich | A61F 2/91 623/1.15 |
| 7,135,038 B1 | 11/2006 | Limon | |
| 7,147,660 B2 | 12/2006 | Chobotov et al. | |
| 7,163,552 B2 | 1/2007 | Diaz | |
| 7,163,553 B2 | 1/2007 | Limon | |
| 7,169,165 B2 | 1/2007 | Belef et al. | |
| 7,169,170 B2 | 1/2007 | Widenhouse | |
| 7,169,172 B2 | 1/2007 | Levine et al. | |
| 7,169,174 B2 | 1/2007 | Fischell et al. | |
| 7,169,175 B2 * | 1/2007 | Cottone, Jr. | A61F 2/88 623/1.2 |
| 7,169,178 B1 | 1/2007 | Santos et al. | |
| 7,175,650 B2 | 2/2007 | Ruetsch | |
| 7,175,655 B1 | 2/2007 | Molaei | |
| 7,179,286 B2 * | 2/2007 | Lenz | A61F 2/91 623/1.15 |
| 7,179,289 B2 | 2/2007 | Shanley | |
| 7,186,263 B2 | 3/2007 | Golds et al. | |
| 7,208,009 B2 * | 4/2007 | Richter | A61F 2/91 248/571 |
| 7,217,286 B2 * | 5/2007 | Falotico | A61F 2/91 623/1.42 |
| 7,243,408 B2 | 7/2007 | Vietmeier et al. | |
| 7,556,644 B2 * | 7/2009 | Burpee | A61F 2/88 623/1.22 |
| 7,637,939 B2 * | 12/2009 | Tischler | A61F 2/91 623/1.15 |
| 7,740,654 B2 | 6/2010 | Kveen et al. | |
| 7,803,180 B2 * | 9/2010 | Burpee | A61F 2/88 623/1.15 |
| 7,988,723 B2 * | 8/2011 | Beach | A61F 2/915 623/1.15 |
| 8,500,794 B2 * | 8/2013 | Beach | A61F 2/915 623/1.15 |
| 8,668,731 B2 | 3/2014 | Kveen et al. | |
| 8,956,400 B2 * | 2/2015 | Beach | A61F 2/91 623/1.15 |
| 8,986,367 B2 | 3/2015 | Kveen et al. | |
| 2001/0039447 A1 * | 11/2001 | Pinchasik | A61F 2/91 623/1.15 |
| 2001/0056296 A1 | 12/2001 | Sugita et al. | |
| 2002/0002400 A1 | 1/2002 | Drasler et al. | |
| 2002/0042646 A1 | 4/2002 | Wall | |
| 2002/0055770 A1 * | 5/2002 | Doran | A61F 2/91 623/1.15 |
| 2002/0082682 A1 * | 6/2002 | Barclay | A61F 2/88 623/1.22 |
| 2002/0095207 A1 * | 7/2002 | Moriuchi | A61F 2/91 623/1.15 |
| 2002/0143390 A1 * | 10/2002 | Ishii | A61F 2/91 623/1.15 |
| 2002/0165603 A1 | 11/2002 | Thornton et al. | |
| 2002/0193868 A1 | 12/2002 | Mitelberg et al. | |
| 2003/0050690 A1 * | 3/2003 | Kveen | A61F 2/91 623/1.15 |
| 2003/0097172 A1 | 5/2003 | Shalev et al. | |
| 2003/0114920 A1 * | 6/2003 | Caro | A61F 2/88 623/1.15 |
| 2003/0144729 A1 * | 7/2003 | Bicek | A61F 2/91 623/1.16 |
| 2003/0149473 A1 * | 8/2003 | Chouinard | A61F 2/91 623/1.15 |
| 2003/0149474 A1 | 8/2003 | Becker | |
| 2003/0195609 A1 * | 10/2003 | Berenstein | A61F 2/856 623/1.15 |
| 2003/0204244 A1 * | 10/2003 | Stiger | A61F 2/90 623/1.16 |

(56) References Cited

U.S. PATENT DOCUMENTS

| | | |
|---|---|---|
| 2003/0229390 A1* | 12/2003 | Ashton ............... A61K 9/0024 623/1.15 |
| 2004/0002753 A1* | 1/2004 | Burgermeister ......... A61F 2/91 623/1.15 |
| 2004/0020663 A1 | 2/2004 | Jackson et al. |
| 2004/0034402 A1* | 2/2004 | Bales ..................... A61F 2/91 623/1.2 |
| 2004/0088044 A1* | 5/2004 | Brown .................... A61F 2/91 623/1.16 |
| 2004/0122504 A1 | 6/2004 | Hogendijk |
| 2004/0147998 A1 | 7/2004 | Nolting |
| 2004/0149294 A1* | 8/2004 | Gianchandani ......... B23H 9/00 128/879 |
| 2004/0158306 A1 | 8/2004 | Mitelberg et al. |
| 2004/0172123 A1* | 9/2004 | Lootz .................... A61F 2/91 623/1.15 |
| 2004/0186556 A1* | 9/2004 | Hogendijk .............. A61F 2/88 623/1.16 |
| 2004/0193209 A1 | 9/2004 | Pavcnik et al. |
| 2004/0215325 A1* | 10/2004 | Penn ..................... A61F 2/91 623/1.15 |
| 2004/0236401 A1 | 11/2004 | Shin et al. |
| 2004/0260384 A1 | 12/2004 | Allen |
| 2005/0015136 A1* | 1/2005 | Ikeuchi .................. A61F 2/91 623/1.15 |
| 2005/0033261 A1 | 2/2005 | Falotico et al. |
| 2005/0033410 A1* | 2/2005 | Hogendijk .............. A61F 2/07 623/1.15 |
| 2005/0038495 A1 | 2/2005 | Greenan |
| 2005/0070992 A1 | 3/2005 | Bolduc et al. |
| 2005/0080479 A1 | 4/2005 | Feng et al. |
| 2005/0085842 A1 | 4/2005 | Eversull et al. |
| 2005/0085899 A1 | 4/2005 | Thornton |
| 2005/0090888 A1 | 4/2005 | Hines et al. |
| 2005/0096725 A1 | 5/2005 | Pomeranz et al. |
| 2005/0096727 A1 | 5/2005 | Allen et al. |
| 2005/0096732 A1 | 5/2005 | Marotta et al. |
| 2005/0113903 A1* | 5/2005 | Rosenthal .............. A61F 2/90 623/1.15 |
| 2005/0125025 A1 | 6/2005 | Rioux |
| 2005/0131426 A1 | 6/2005 | Moctezuma de la Barrera et al. |
| 2005/0131529 A1 | 6/2005 | Cragg |
| 2005/0131530 A1 | 6/2005 | Darack |
| 2005/0149164 A1 | 7/2005 | Rivelli, Jr. et al. |
| 2005/0165469 A1* | 7/2005 | Hogendijk .............. A61F 2/88 623/1.15 |
| 2005/0192661 A1 | 9/2005 | Griffen et al. |
| 2005/0216076 A1* | 9/2005 | Kveen .................... A61F 2/91 623/1.22 |
| 2005/0246010 A1 | 11/2005 | Alexander et al. |
| 2006/0012922 A1 | 1/2006 | Shoji |
| 2006/0015171 A1 | 1/2006 | Armstrong |
| 2006/0020322 A1* | 1/2006 | Leynov ................... A61F 2/91 623/1.15 |
| 2006/0025849 A1 | 2/2006 | Kaplan et al. |
| 2006/0030932 A1 | 2/2006 | Kantor et al. |
| 2006/0030934 A1* | 2/2006 | Hogendijk .............. A61F 2/07 623/1.22 |
| 2006/0060266 A1 | 3/2006 | Bales et al. |
| 2006/0064154 A1 | 3/2006 | Bales et al. |
| 2006/0064158 A1 | 3/2006 | Bales et al. |
| 2006/0074480 A1 | 4/2006 | Bales et al. |
| 2006/0079955 A1 | 4/2006 | Brown |
| 2006/0142832 A1 | 6/2006 | Schmitt |
| 2006/0155312 A1 | 7/2006 | Levine et al. |
| 2006/0173490 A1 | 8/2006 | LaFontaine et al. |
| 2006/0184226 A1 | 8/2006 | Austin |
| 2006/0195137 A1 | 8/2006 | Sepetka et al. |
| 2006/0206002 A1 | 9/2006 | Frassica et al. |
| 2006/0247759 A1* | 11/2006 | Burpee ................... A61F 2/88 623/1.15 |
| 2006/0252624 A1 | 11/2006 | Kuribayashi et al. |
| 2007/0005126 A1 | 1/2007 | Tischler |
| 2007/0027522 A1 | 2/2007 | Chang et al. |
| 2007/0055365 A1 | 3/2007 | Greenberg et al. |
| 2007/0129786 A1* | 6/2007 | Beach ..................... A61F 2/91 623/1.15 |
| 2007/0208416 A1* | 9/2007 | Burpee ................... A61F 2/88 623/1.22 |
| 2009/0036976 A1* | 2/2009 | Beach ................... A61F 2/915 623/1.22 |
| 2010/0286760 A1* | 11/2010 | Beach ..................... A61F 2/91 623/1.22 |
| 2011/0029064 A1* | 2/2011 | Burpee ................... A61F 2/88 623/1.22 |
| 2011/0245910 A1* | 10/2011 | Beach ................... A61F 2/915 623/1.22 |
| 2014/0379066 A1* | 12/2014 | Burpee ................... A61F 2/88 623/1.11 |
| 2015/0148887 A1* | 5/2015 | Beach ..................... A61F 2/91 623/1.22 |

FOREIGN PATENT DOCUMENTS

| | | |
|---|---|---|
| EP | 0916317 A1 | 5/1999 |
| EP | 0941716 A2 | 9/1999 |
| EP | 0950386 A2 | 10/1999 |
| EP | 0951877 A2 | 10/1999 |
| EP | 1123065 A1 | 8/2001 |
| EP | 1452151 A2 | 9/2004 |
| EP | 1757249 A1 | 2/2007 |
| EP | 2119415 A1 | 11/2009 |
| JP | 2002210021 A | 7/2002 |
| JP | 2002355315 A | 12/2002 |
| WO | 9603092 A1 | 2/1996 |
| WO | WO 96/33671 | 10/1996 |
| WO | 9714375 A1 | 4/1997 |
| WO | 9830172 A1 | 7/1998 |
| WO | 9830173 A1 | 7/1998 |
| WO | 9833546 A1 | 8/1998 |
| WO | 9925272 A1 | 5/1999 |
| WO | 0016718 A1 | 3/2000 |
| WO | 0032136 A1 | 6/2000 |
| WO | 0032138 A1 | 6/2000 |
| WO | 0062711 A1 | 10/2000 |
| WO | 0126584 A1 | 4/2001 |
| WO | 0164133 A1 | 9/2001 |
| WO | 0193777 A2 | 12/2001 |
| WO | 02094127 A2 | 11/2002 |
| WO | 02094128 A2 | 11/2002 |
| WO | 03020102 A2 | 3/2003 |
| WO | 03022172 A2 | 3/2003 |
| WO | 2004110301 A2 | 12/2004 |
| WO | 2005063251 A1 | 7/2005 |
| WO | 2005076691 A2 | 8/2005 |
| WO | 2005120394 A2 | 12/2005 |
| WO | 2006047679 A1 | 5/2006 |

OTHER PUBLICATIONS

CN Search Report dated Apr. 15, 2014 for Chinese Application No. 201110281185.4, filed Apr. 4, 2006.

European Search Report for Application No. EP12171358, mailed on Aug. 31, 2012, 6 pages.

International Search Report and Written Opinion for Application No. PCT/US2006/012579, mailed on Jan. 10, 2008, 6 pages.

Lownie S.P. et al., "Endovascular Theapy of a Large Vertebral Artery Aneurysm Using Stent and Coils," The Canadian journal of neurological sciences, 2000, vol. 27 (2), pp. 162-165.

Pride G.L., et al., "Endovascular Problem Solving With Intravascular Stents," American Journal of Neuroradiology, 2000, vol. 21 (3), pp. 532-540.

Supplementary European Search Report for Application No. EP06740521, mailed Mar. 2, 2010, 7 pages.

(56) References Cited

OTHER PUBLICATIONS

Wanke et al., Treatment of WideNecked Intracranial Aneurysms With a SelfExpanding Stent System: Initial Clinical Experience, AJNR American Journal of Neuroradiology, 24:1192-1199, 2003.

* cited by examiner

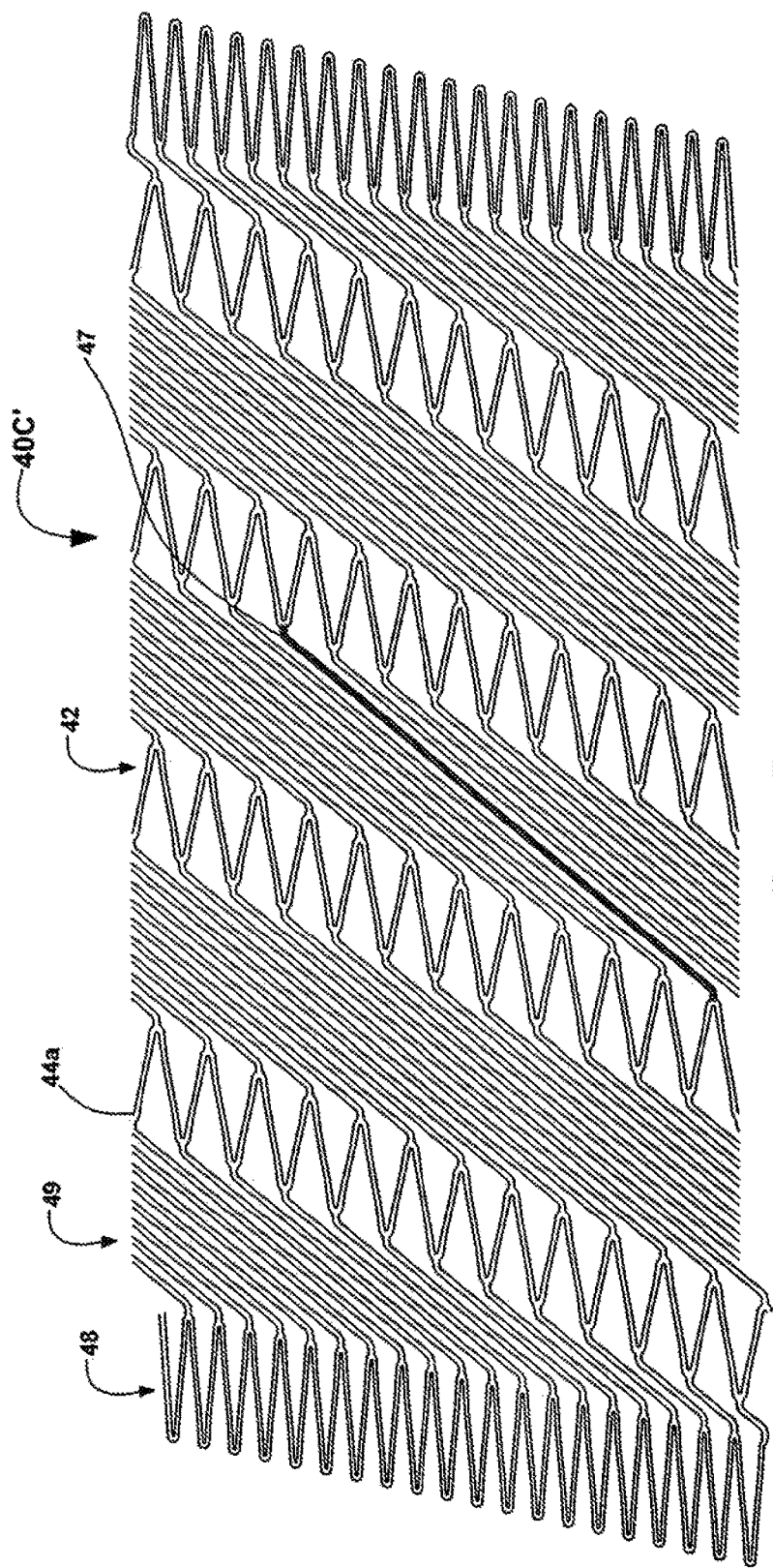

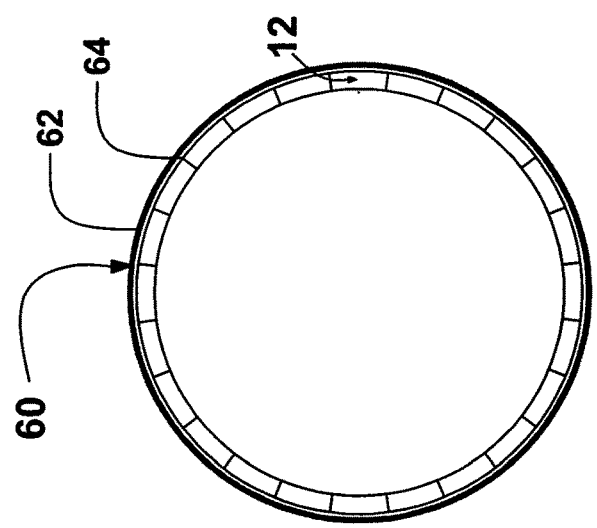
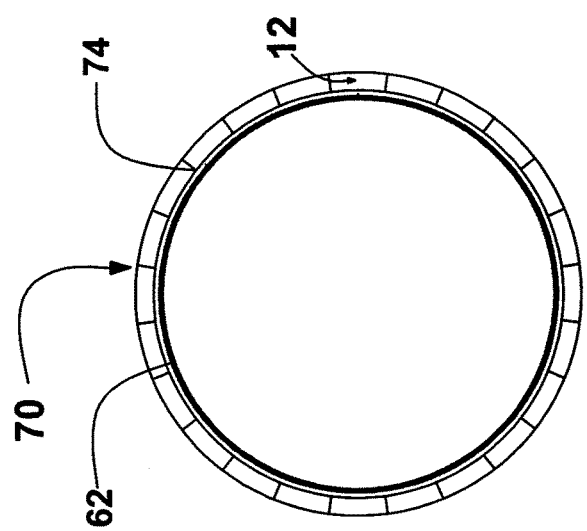
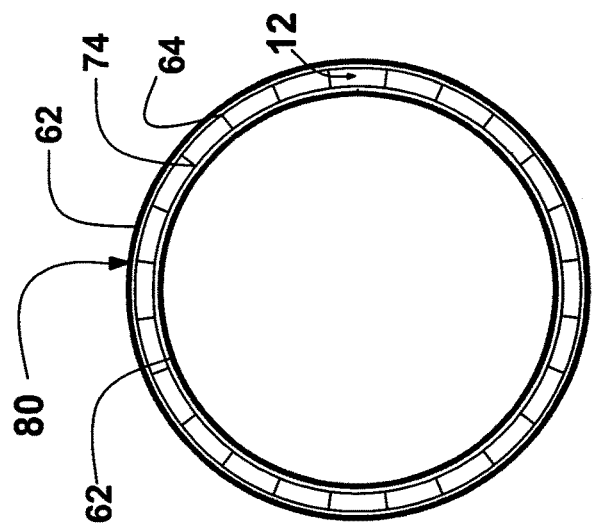

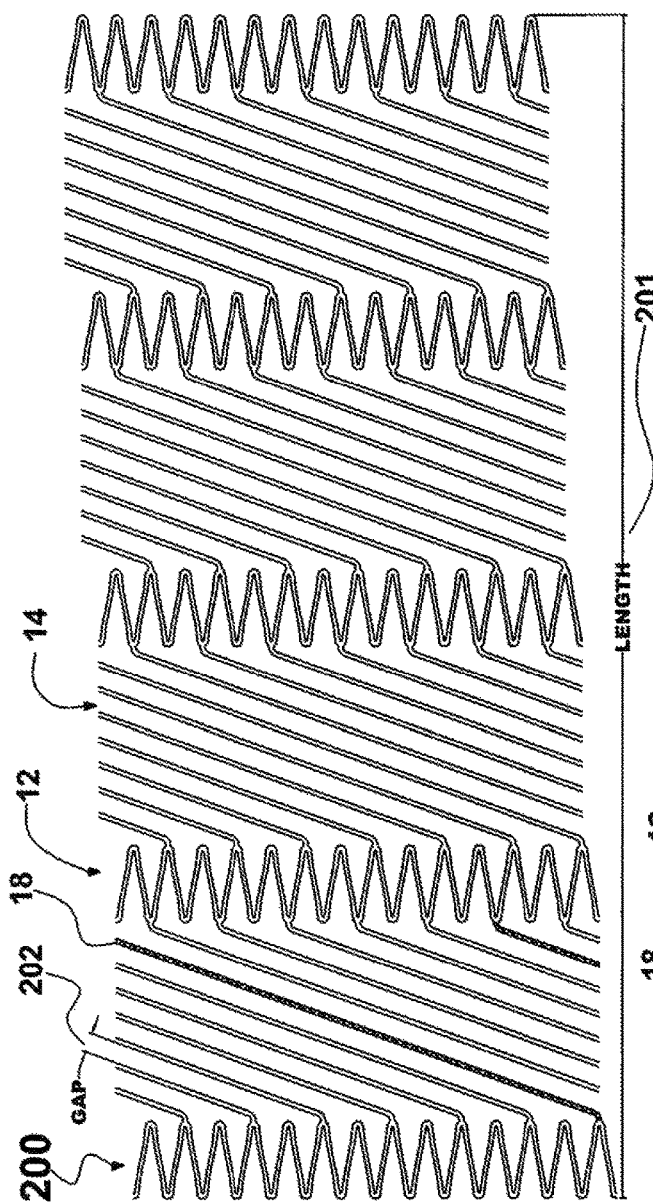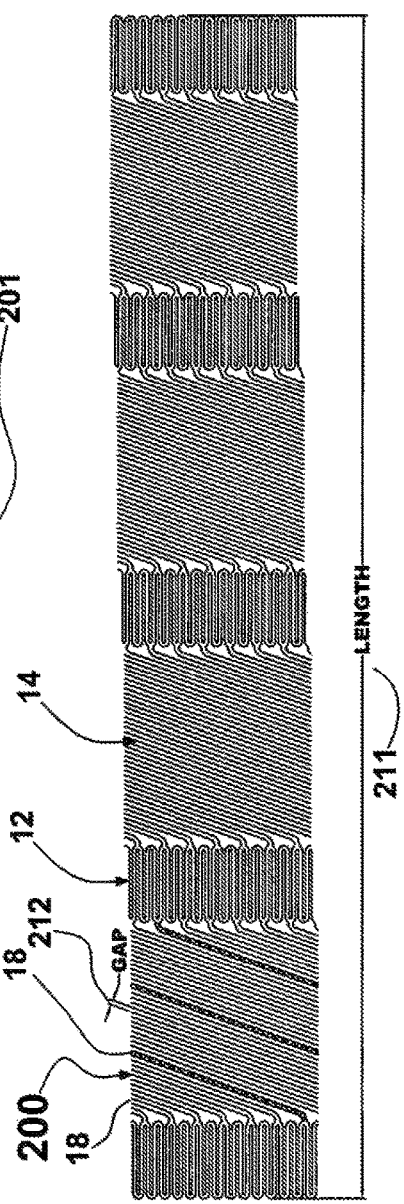

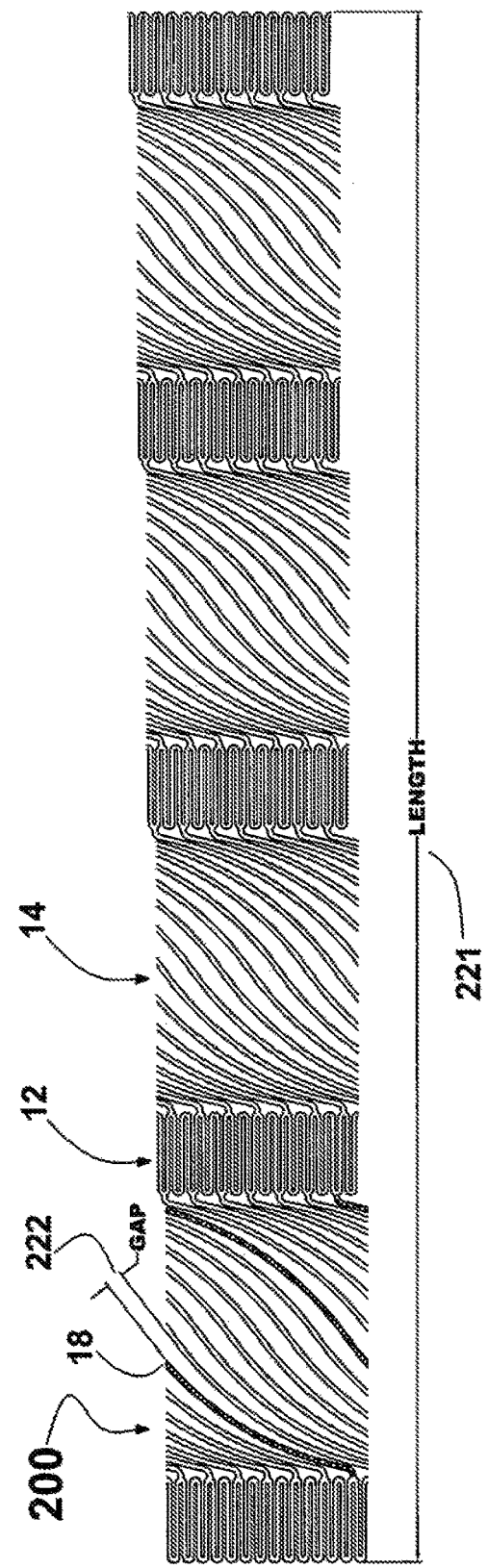

FLEXIBLE STENT

PRIORITY

This application claims priority under 35 USC §§120, 121 and is a divisional application of prior filed U.S. patent application Ser. No. 12/884,514 filed on Sep. 27, 2010, pending, which was a divisional application of prior filed U.S. patent application Ser. No. 11/397,987, filed on Apr. 4, 2006, which was a continuation-in-part of U.S. patent application Ser. No. 11/250,226 filed Oct. 14, 2005 which claims the benefit of U.S. Provisional Patent Application No. 60/667,613 filed Apr. 4, 2005, in which the entirety of all prior filed applications are hereby incorporated by reference into this application as if set forth in full herein.

BACKGROUND

The present invention relates generally to expandable tubular structures capable of insertion into small spaces in living bodies and, more particularly, concerns a stent structure which is capable of substantial and repeated flexing at points along its length without mechanical failures and with no substantial changes in its geometry.

A stent is a tubular structure that, in a radially compressed or crimped state, may be inserted into a confined space in a living body, such as an artery or other vessel. After insertion, the stent may be expanded radially to enlarge the space in which it is located. Stents are typically characterized as balloon-expanding (BX) or self-expanding (SX). A balloon-expanding stent requires a balloon, which is usually part of a delivery system, to expand the stent from within and to dilate the vessel. A self expanding stent is designed, through choice of material, geometry, or manufacturing techniques, to expand from the crimped state to an expanded state once it is released into the intended vessel. In certain situations higher forces than the expanding force of the self expanding stent are required to dilate a diseased vessel. In this case, a balloon or similar device might be employed to aid the expansion of a self expanding stent.

Stents are typically used in the treatment of vascular and non-vascular diseases. For instance, a crimped stent may be inserted into a clogged artery and then expanded to restore blood flow in the artery. Prior to release, the stent would typically be retained in its crimped state within a catheter and the like. Upon completion of the procedure, the stent is left inside the patient's artery in its expanded state. The health, and sometimes the life, of the patient depend upon the stent's ability to remain in its expanded state.

Many available stents are flexible in their crimped state in order to facilitate the delivery of the stent, for example within an artery. Few are flexible after being deployed and expanded. Yet, after deployment, in certain applications, a stent may be subjected to substantial flexing or bending, axial compressions and repeated displacements at points along its length, for example, when stenting the superficial femoral artery. This can produce severe strain and fatigue, resulting in failure of the stent.

A similar problem exists with respect to stent-like structures. An example would be a stent-like structure used with other components in a catheter-based valve delivery system. Such a stent-like structure holds a valve which is placed in a vessel.

SUMMARY OF THE DISCLOSURE

In accordance with the present invention, a stent or a stent-like structure is constructed to have different types of tubular portions along its length. In general, there are strut portions and helical portions, where the strut portions are constructed primarily to provide radial expansion and radial strength, and the helical portions are constructed primarily to permit repeated flexing and axial compression and expansion. The flexing and axial compression are likely to be required simultaneously, so the stent structure permits repeated and substantial flexing while in an axially compressed or expanded state, and it permits axial compression while in a flexed state. Preferably, strut portions are provided between helical portions or helical portions are provided between strut portions. In a preferred embodiment, the stent is self-expanding and strut portions and helical portions alternate along the length of the stent.

The stent is preferably constructed so that, in the expanded state the helical portions permit axial compression or expansion of about 20% (preferably between 15% and 25%) and simultaneously permit bending with a minimum bending radius of about 13 mm (preferably between 10 mm and 16 mm).

In accordance with another aspect of the invention, a helical portion is made of helical elements which extend helically about the axis of the stent between points on two different strut portions which are spaced apart circumferentially by a distance which is more than approximately 25% of the circumference of the stent (which is equivalent to an extent of 90 degrees about the axis of the stent) when it is in its expanded state.

In accordance with yet another aspect of the invention, a helical portion is made of helical elements which extend helically about the axis of the stent between locations on two different strut portions. In one embodiment a helical element is bi-directional, in that it extends first in one circumferential direction and then the other between the two locations and has a peak.

In accordance with yet another aspect of the invention, a stent has a plurality of axially spaced strut portions defining generally tubular axial segments of the stent and constructed to be radially expandable. A helical portion is interposed axially between two strut portions, and the helical portion has a plurality of helical elements connected between circumferentially spaced locations on two strut portions. A helical element extends helically between these locations, and at least part of the helical portion has a greater diameter than a strut portion when the stent is in an expanded state. In an alternate embodiment, at least part of the helical portion has a smaller diameter than the strut portion when the strut is in an expanded state.

In one embodiment, the helical element is wound at least 90 degrees between strut elements connected to the helical element. In another embodiment, the helical element is wound at least 360 degrees between strut elements connected to the helical element.

In an alternate embodiment, stent grafts are formed of a biocompatible graft material covering the outside, inside or both the outside and inside of the stent. The stent graft can have any embodiment of a stent structure of the present invention. Stent graft devices are used, for example, in the treatment of aneurysms, dissections and tracheo-bronchial strictures. The stent can also be coated with a polymer and/or drug eluting material as are known in the art.

BRIEF DESCRIPTION OF THE DRAWINGS

The foregoing description, as well as further objects, features, and advantages of the present invention will be understood more completely from the following detailed description of presently preferred, but nonetheless illustrative embodiments in accordance with the present invention, with reference being had to the accompanying drawings, in which:

FIG. 7B is a plan view of another embodiment of the stent in accordance with the present invention;

FIG. 10A is a sectional end view of an alternate embodiment of a stent in accordance with the present invention including graft material covering an outer surface of the stent;

FIG. 10B is a sectional end view of an alternate embodiment of a stent in accordance with the present invention including graft material covering an inner surface of the stent;

FIG. 10C is a sectional end view of an alternate embodiment of a stent in accordance with the present invention including graft material covering an outer surface and an inner surface of the stent;

FIG. 12A is a plan view of an alternate embodiment of a stent in an expanded state;

FIG. 12B is a plan view of the stent of FIG. 12A in a crimped state such that the gap between helical elements is the same throughout the helical portions. Additionally, the length of the stent is the same in both the crimped and expanded state;

FIG. 12C is a plan view of the stent of FIG. 12A in a crimped state such that the gap between helical elements changes throughout the helical portion. Additionally, the stent is longer in the crimped state than the expanded state.

MODES OF CARRYING OUT THE INVENTION

Figure 1A:
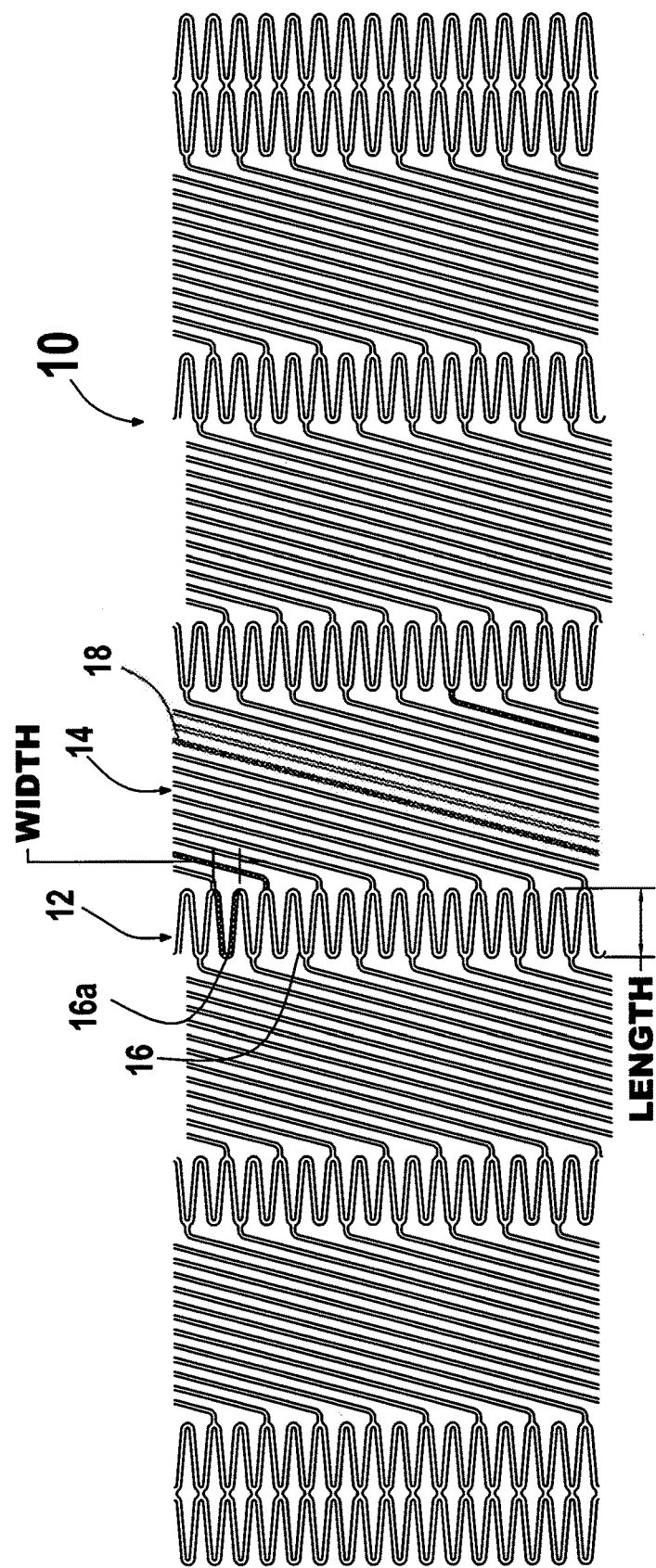
FIG. 1A is a plan view of a first embodiment of a stent in accordance with the present invention, the stent being shown in an unexpanded state.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 1B:
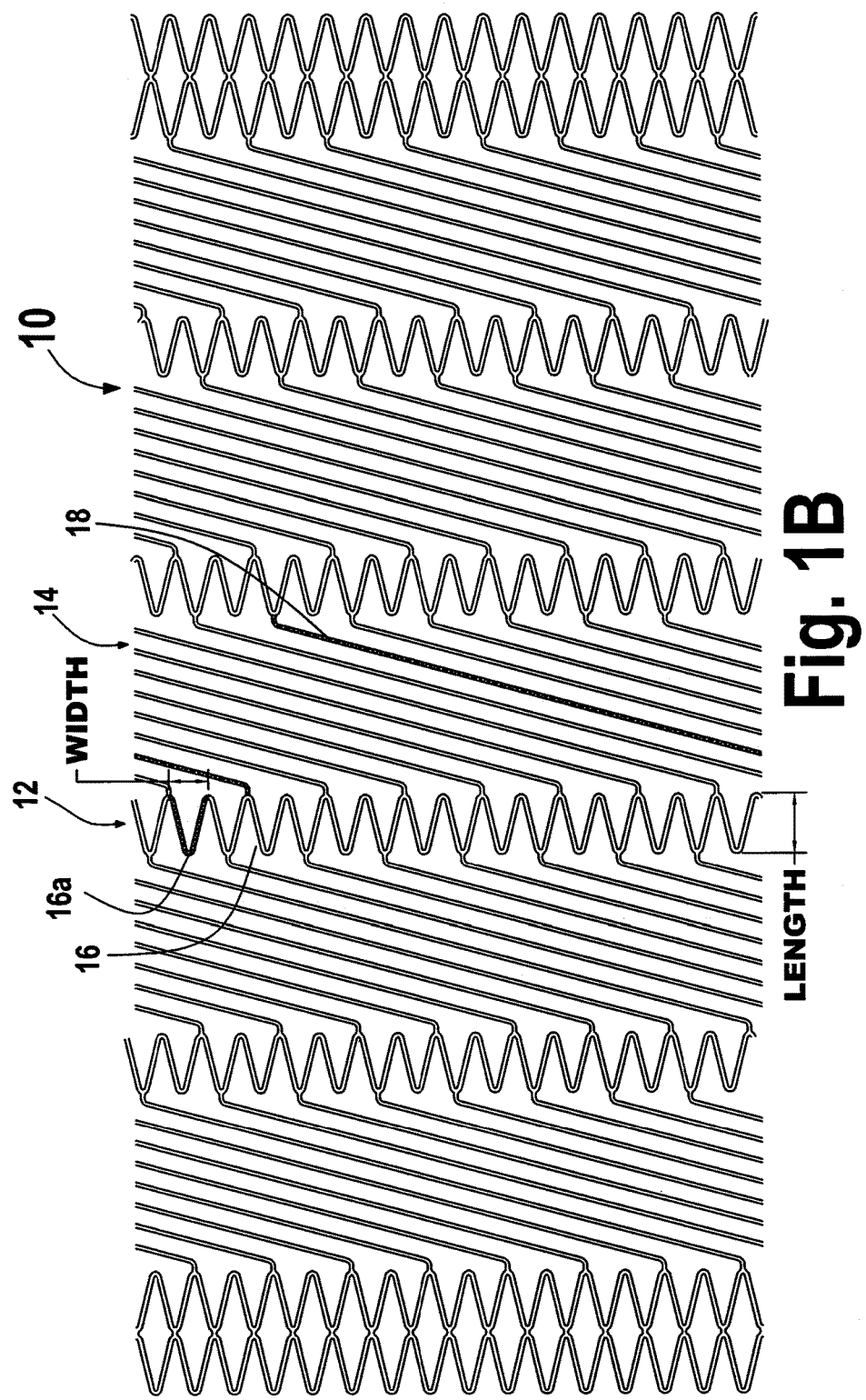
FIG. 1B is a plan view of the first embodiment of a stent in accordance with the present invention, the stent being shown in a radially expanded state.

FIGS. 1A and 1B are plan views of a first embodiment of stent 10 in accordance with the present invention shown in an unexpanded state and expanded state, respectively. As used herein, the term "plan view" will be understood to describe an unwrapped plan view. This could be thought of as slicing open a tubular stent along a line parallel to its axis and laying it out flat. It should therefore be appreciated that, in the actual stent, the top edge of the FIG. 1A will be joined to the lower edge.

Stent 10 is made from a common material for self expanding stents, such as Nitinol nickel-titanium alloy (Ni/Ti), as is well known in the art. Typically, the stent is laser cut from tubing, for example, with a diameter of about 5 mm (FIG. 1A). It is then expanded and set to a diameter of about 8 mm (FIG. 1B), and for pre-deployment it would be crimped to a diameter appropriate for the application, for example about 3 mm. However, it is contemplated that the present invention is applicable to any type and size of stent.

Stent 10 is generally made up of strut portion 12 and helical portion 14 with axially aligned strut portion 12 alternating with helical portion 14. In a preferred embodiment, strut portion 12 is positioned at either end of stent 10. Strut portion 12 being radially expandable upon deployment. Each strut portion 12 includes strut ring 16 having a pattern of wave-like strut elements 16a that progresses circumferentially about the stent. Each strut element 16a has a width equal to the peak to peak distance around the stent and a length equal to the peak-to-peak distance along the length of the stent. It will be appreciated that strut ring 16 could be partially straightened (stretched vertically in FIG. 1B) so as to widen strut elements 16a and reduce their length. This is equivalent to expanding stent 10 radially. Preferably, the material of which stent 10 is made is such that strut element 16a will retain some wave-like shape in a radially expanded state. For delivery, the stent would be crimped and fitted into a catheter, and it would expand after the catheter is inserted into the vessel and the stent is advanced out of the catheter.

Each helical portion is made up of a plurality of side-by-side helical elements 18, each of which is helically wound about an axis of stent 10. Helical portion 14 is expandable radially upon deployment and compressible, expandable and bendable in a deployed state. Helical elements 18 can be connected between opposed individual wave portions of strut element 16a of different strut portions 12. In this embodiment, each helical element 18 makes a complete rotation about the surface of stent 10. However, they can make a partial rotation or more than one rotation. The helical portion is preferably constructed to permit repeated axial compression or expansion of about 20% (preferably between 15% and 25%) and simultaneously permit bending with a minimum bending radius of about 13 mm (preferably between 10 mm and 16 mm), all without failure.

Improved flexibility and axial compression can generally be accomplished if helical element 18 is wound at least 90 degrees between strut elements 16a connected to helical elements 18. Alternatively, helical element 18 is wound at least 360 degrees between strut elements 16a connected to helical elements 18.

Figure 2:
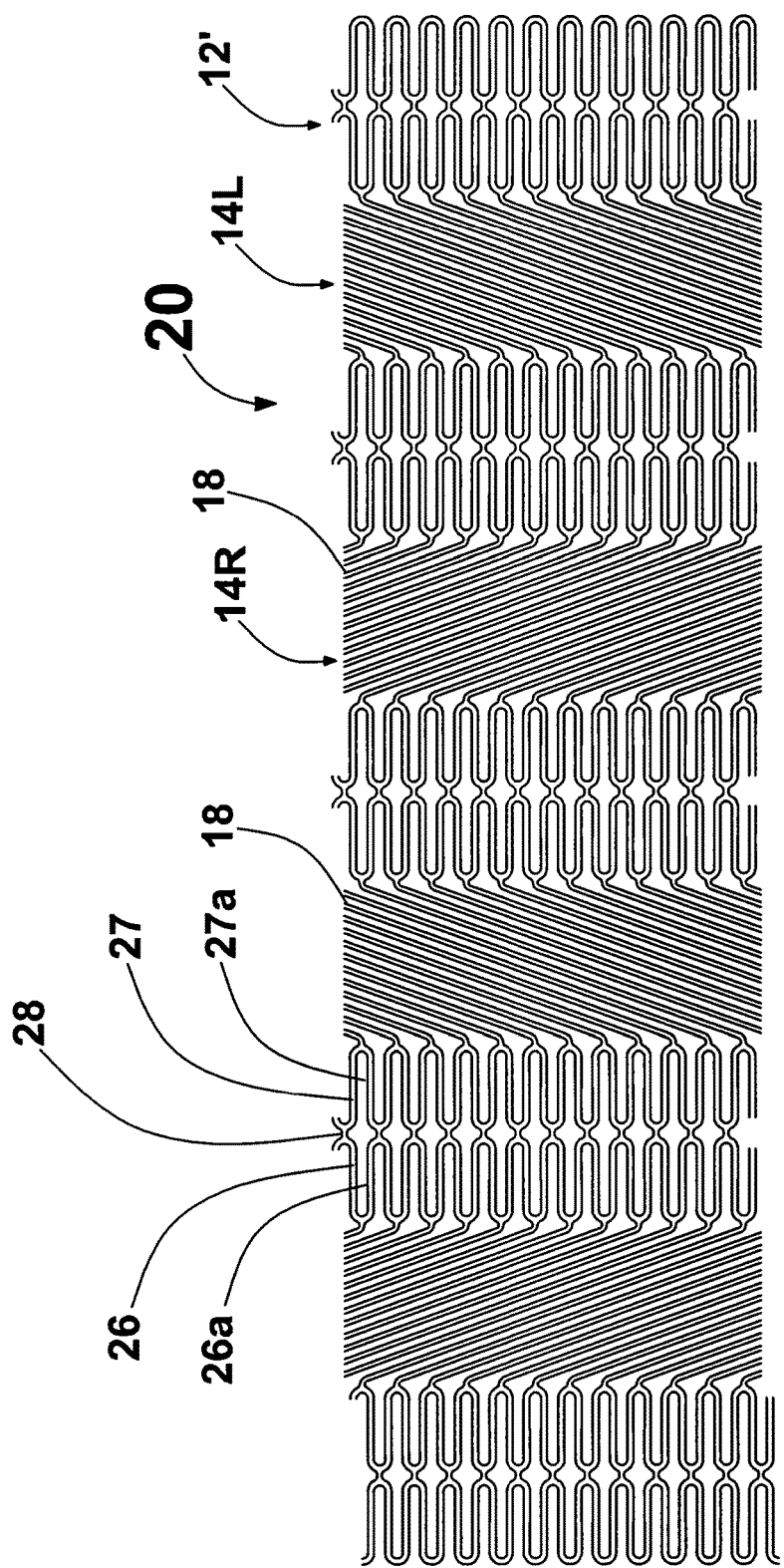
FIG. 2 is a plan view of a second embodiment of a stent in accordance with the present invention.

FIG. 2 is a plan view of a second embodiment of stent 20 similar to stent 10 of FIG. 1. The primary differences are in the structure of strut portions 12' and that there are right-handed and left-handed helical portions (14R and 14L, respectively). Each strut portion 12' comprises two adjacent strut rings 26, 27 connected by short link 28. The closely opposed peaks of strut elements 26a, 27a are connected by short link 28, so that each strut portion 12' has a double strut ring structure. It would also be possible to connect multiple strut rings together to form a larger strut portion. The advantage of twin or multiple strut ring strut portions is that they offer increased radial stiffness over the single strut ring strut portion and can stabilize the strut portions so they are less affected by axial forces.

In a right-handed helical portion 14R, the elements 18 progress clockwise about the surface of stent 10 and, in a left-handed helical portion 14L, they progress counterclockwise. Helical elements 18 essentially float and permit relatively large displacements about and along the stent axis between the two strut ring portions at either end. In this embodiment, it will be appreciated that the diameter of the stent at each helical portion 14R, 14L is the same as the diameter of the stent at the strut portions 12 on either side. However, this need not be the case, as will become evident from additional embodiments discussed below. A benefit of using left-handed and right-handed helical portions is that when the stent deploys the two portions rotate in opposite directions, maintaining the relative rotational positions of different axial portions of the stent.

Figure 3:
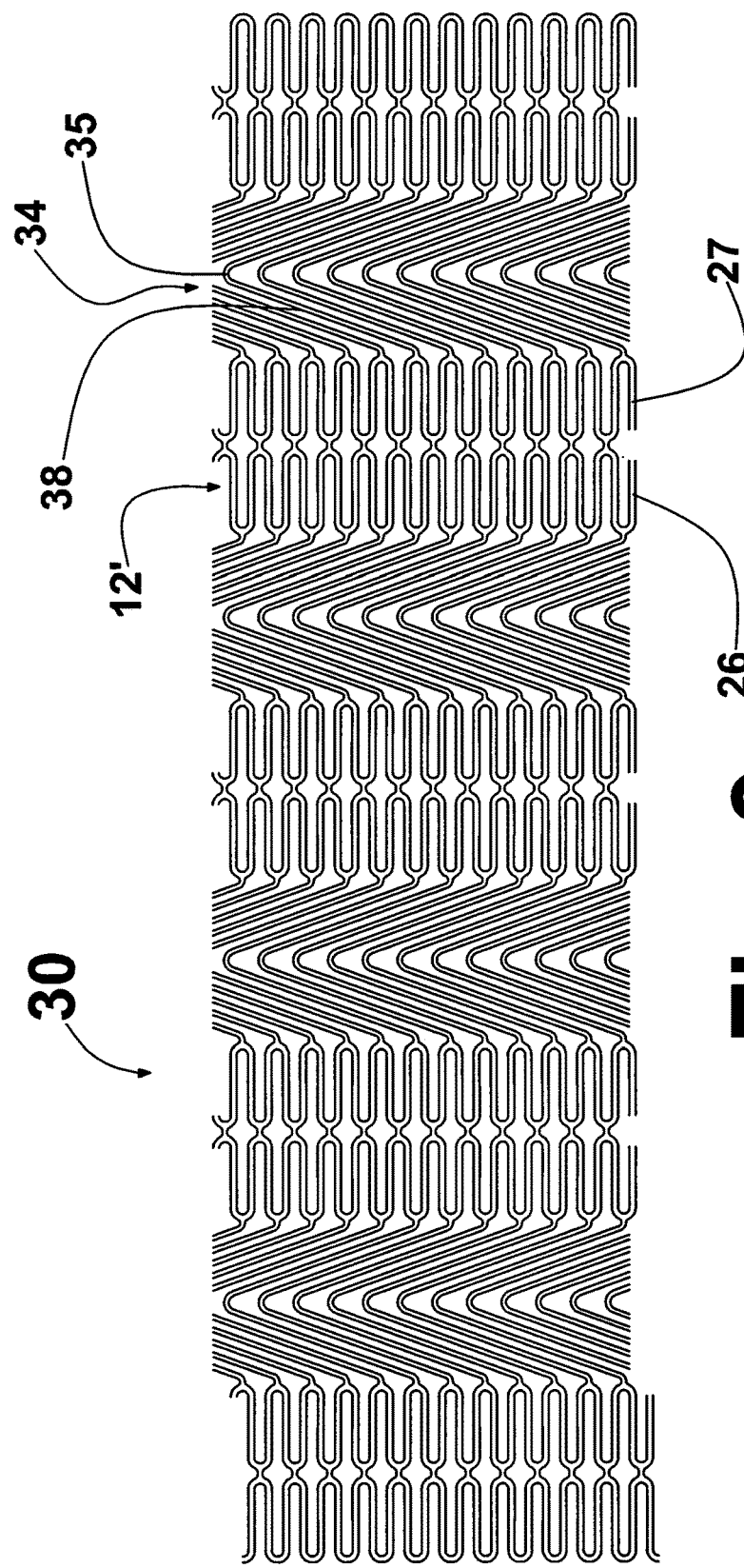
FIG. 3 is a plan view of a third embodiment of a stent in accordance with the present invention.

FIG. 3 is another embodiment of stent 30 in accordance with the present invention. It is similar to stent 20 of FIG. 2, except that helical portions 34 include helical element 38 which progresses bi-directionally (first counterclockwise and then clockwise) about the perimeter of stent 30 between connection locations on two different strut portions 12'. Helical element 38 is wound at least 90 degrees from a first strut portion 12' to peak 35 and is wound 90 degrees from peak 35 to a second strut portion 12' in order to maintain flexibility. The one-directional helical elements 18 of FIGS. 1A and 1B can allow adjacent strut portions to rotate relative to one another. The bi-directional helical elements 38 limit the amount adjacent strut portions can rotate about the stent axis relative to one another but still provide axial and bending flexibility.

Figure 4:
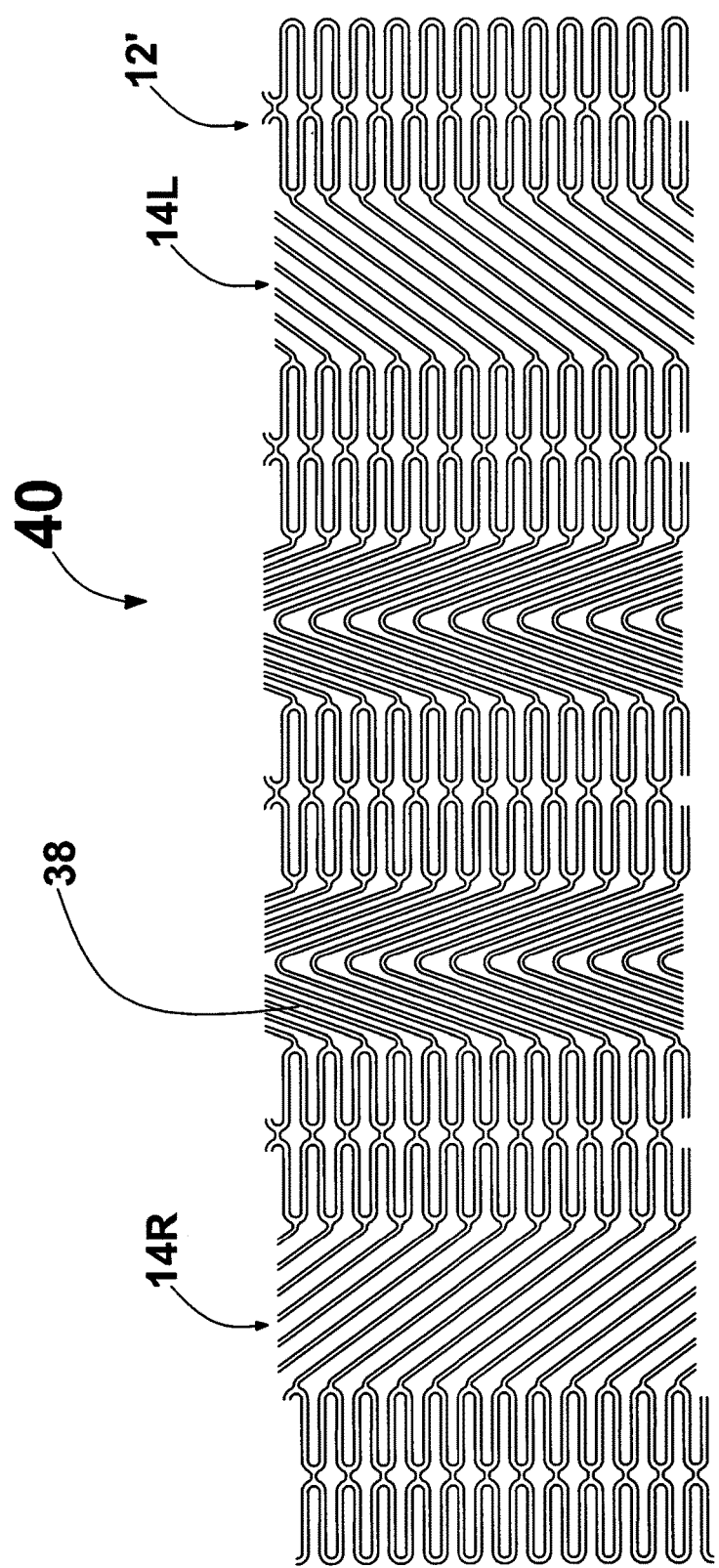
FIG. 4 is a plan view of a fourth embodiment of a stent in accordance with the present invention.

FIG. 4 is a plan view of a fourth embodiment of a stent in accordance with the present invention. In this case, stent 40 has strut portions 12' of FIG. 2 and the helical portions 14L, 14R (FIG. 2) and helical portions 34 (FIG. 3). The advantage of this construction is that combining different types of helical elements allows a mix of properties as described herein, providing the opportunity for further optimization of overall stent performance for a given application.

Figure 5:
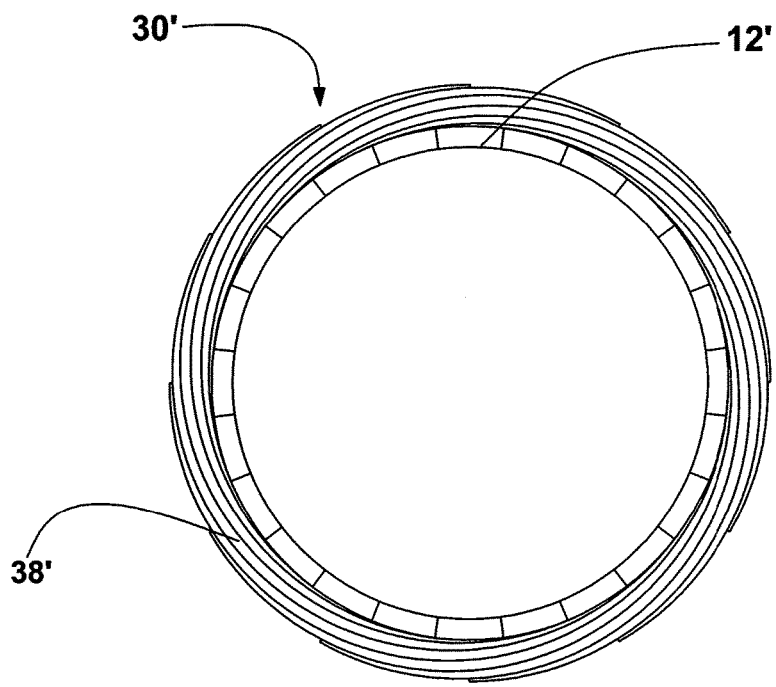
FIG. 5 is a sectional end view of a fifth embodiment of a stent in accordance with the present invention.
Figure 6:
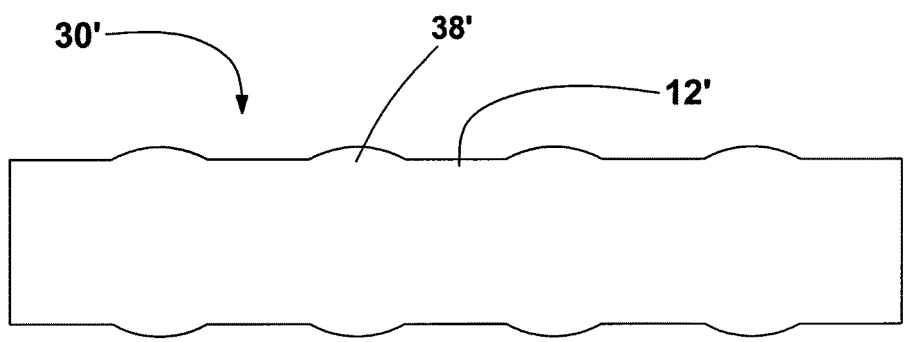
FIG. 6 is a lengthwise side outline view of the same embodiment as FIG. 5.

FIG. 5 is a sectional view perpendicular to the axis of a fifth embodiment of stent 30' in accordance with the present invention, and FIG. 6 is a side outline view of the same embodiment. The stent has the structure shown in FIG. 3, except that helical portions 38' have a larger diameter than strut portions 12'. In this construction the radial stiffness of the helical portions is increased, but to a lesser degree than the strut portions.

When all portions of the stent have the same diameter, the helical portions may not have as much outward force on a vessel as the strut portions when the strut is expanded. The geometry of FIG. 6 will tend to force the helical portions to expand more than the strut portions, increasing the outward force of the helical portions, which equalizes the radial stiffness.

Nitinol structures have a biased stiffness, such that the force required to collapse the structure back towards the collapsed state is generally greater than the force that continues to dilate the diseased vessel when the stent is in its expanded state. With some self expanding Nitinol stents, a balloon is used to assist the expansion/dilation of the vessel. The biased stiffness is enough to support the open vessel, but the outward force may not be enough to open the vessel (or it may take a longer period of time). A stent with the type of geometry shown in FIG. 5 would therefore be a good expedient to use in conjunction with balloon assisted expansion, or other applications requiring additional expansive force.

Figure 7A:
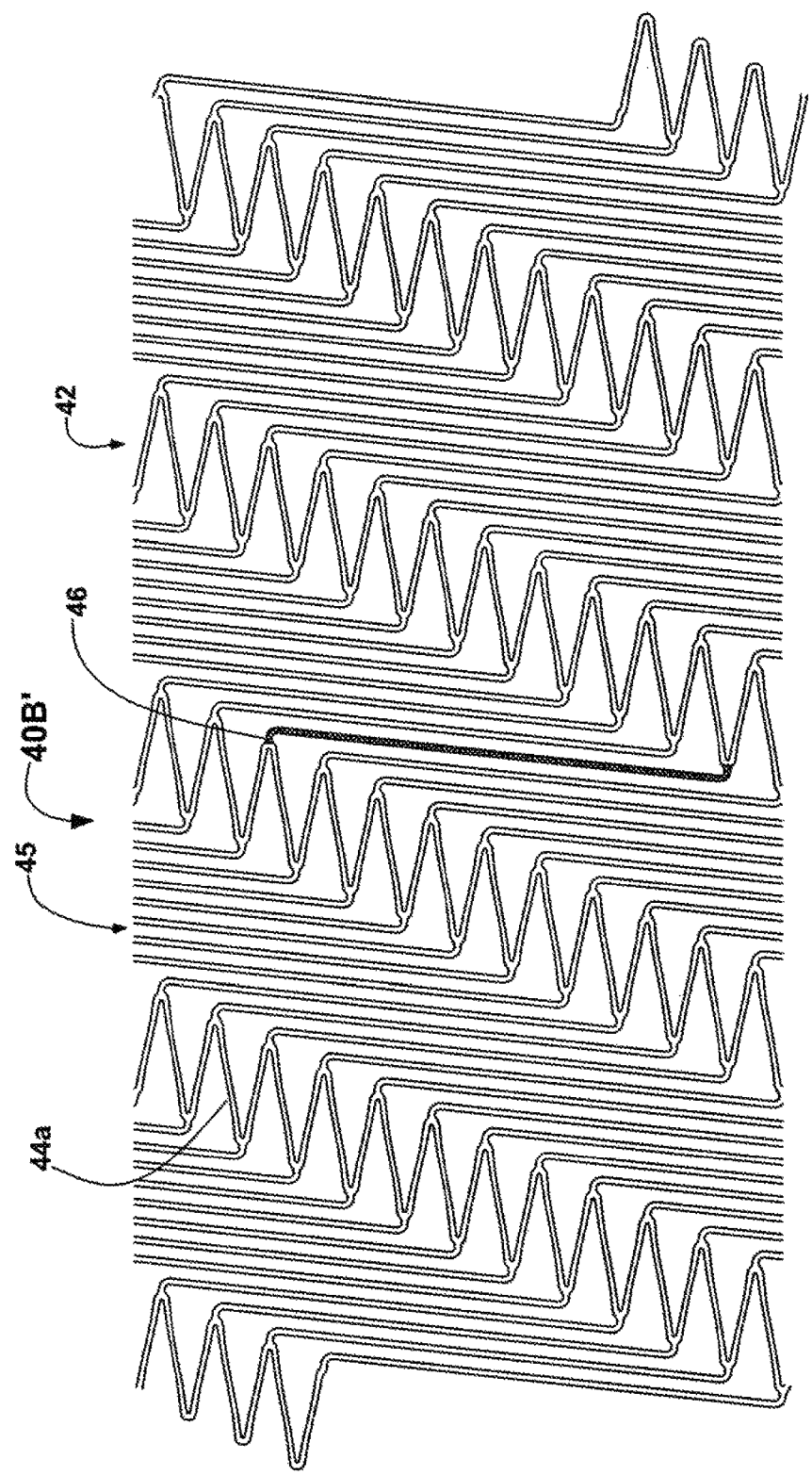
FIG. 7A is a plan view of another embodiment of a stent in accordance with the present invention.

FIG. 7A is a plan view of another embodiment of stent 40B' in accordance with the present invention. Stent 40B' includes strut member 42. Strut member 42 progresses helically from one end of stent 40B' to the other. Strut member 42 forms main body of stent 40B'. In this embodiment, each strut element 44a is connected to a strut in a subsequent winding of strut member 42 by helical element 46. In this embodiment, helical element 46 of helical portion 45 progresses helically less than one full rotation of 360 degrees about stent 40B'. Helical element 46 progresses in a direction opposite of the direction of which strut member 42 progresses helically about stent 40B'.

Preferably, helical elements 46 are axially abutted, forming a type of spring which permits a great deal of flexibility and axial expansion, while strut member 42 provides radial strength and retains the stent in its expanded condition.

FIG. 7B is a plan view of another embodiment of stent 40C' in accordance with the present invention. Stent 40C' is similar to stent 40B' and includes strut member 42. Strut member 42 progresses helically from one end of stent 40C' to the other. Strut member 42 forms main body of stent 40C'. In the present embodiment, each strut element 44a is connected to a strut in a subsequent winding of strut member 42 by helical element 47. In this embodiment, helical element 47 progresses helically about stent 40C' in the same direction as strut member 42 progresses helically about stent 40C'. Stent 40C' includes transitional helical portions 49 and strut portions 48 at either end of stent 40C' to allow strut portion 48 to be provided at either end of stent 40C'.

Stents 40B' and 40C' have the advantage that the flexible helical elements are distributed more continuously along the length of the stent and may provide more continuous flexibility.

Those skilled in the art will appreciate that various modifications to stent 40B' or 40C' are possible, depending upon the requirements of a particular design. For example, it might be desirable to connect fewer than all of strut elements 44a in a particular winding to a subsequent winding, reducing the number of helical elements 46. Helical elements 46 can extend for less or for any integer or non-integer multiple of a rotation. A stent could also be made of a plurality of tubular sections each having the construction of stent 40B' or 40C' and joined lengthwise by another type of section.

Figure 8:
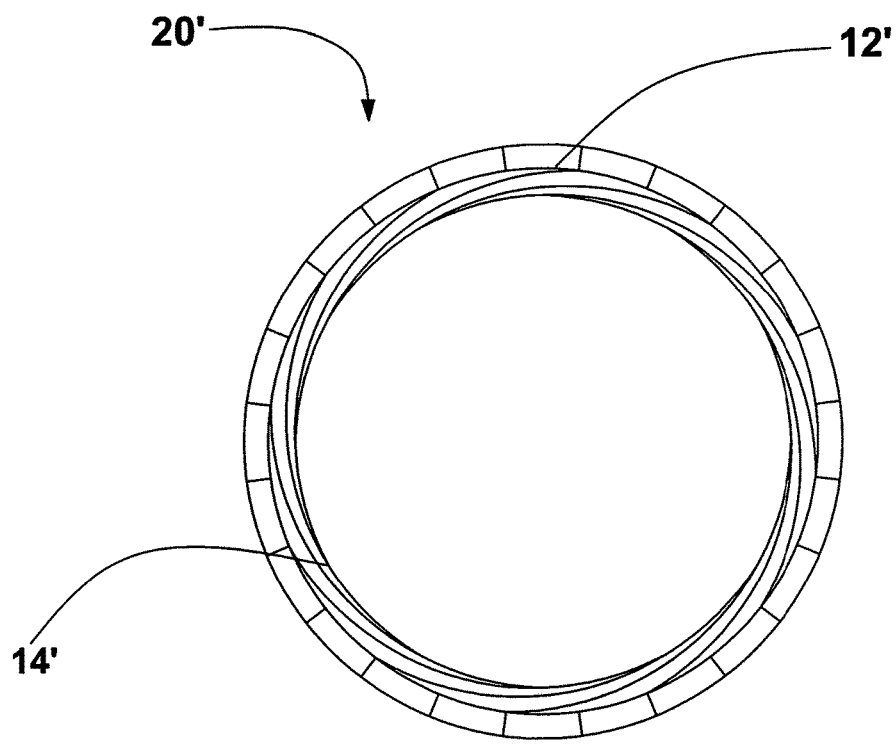
FIG. 8 is a sectional end view of another embodiment of the stent in accordance with the present invention.
Figure 9:
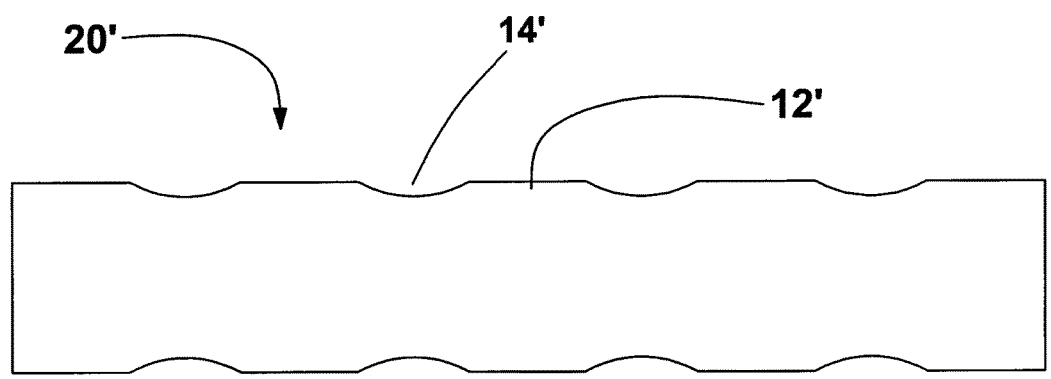
FIG. 9 is a lengthwise side outline view of the embodiment shown in FIG. 8.

FIG. 8 is a sectional view perpendicular to the axis of an embodiment of stent 20' in accordance with the present invention, and FIG. 9 is a side outline view of the same embodiment. The stent has the structure shown in FIG. 1A, except that helical portions 14' neck down to a smaller diameter than strut portions 12'. In this construction the helical portions will exert less force on the vessel wall than if the helical portions were the same diameter. Reducing the force the stent exerts on a vessel wall can reduce the amount of damage done to a vessel and provide a better performing stent.

FIGS. 10A-10C are sectional views perpendicular to the axis of the stent in accordance with the present invention. Stent graft 60, 70 and 80 have a stent structure of the present invention of any of the embodiments described above with helical portions interposed between strut portions. In one embodiment, biocompatible graft material 62 covers outside 64 of stent graft 60, as shown in FIG. 10A. Alternatively, biocompatible graft material 62 covers inside 74 of stent 70, as shown in FIG. 10B. Alternatively, graft material 62 covers outside 64 and inside 74 of stent 80, as shown in FIG. 10C. Graft material 62 can be formed of any number of polymers or other biocompatible materials that have been woven or formed into a sheet or knitted surface. Alternatively, the stent can be coated with a polymer and/or drug eluting material as are known in the art.

FIGS. 11A-11J are side profile views of stent grafts including the features of the flexible stent structure of the present invention.

Figure 11A:
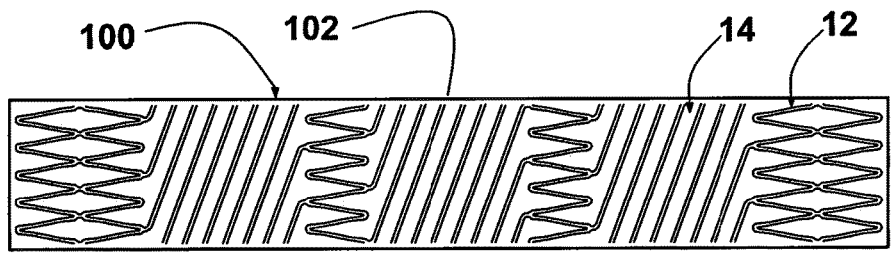
FIG. 11A is a side view of an alternate embodiment of a stent in accordance with the present invention including graft material attached to the strut portion, the graft material covering the strut portion and the helical portion.

Stent graft 100 comprises a continuous covering of graft material 102 covering stent 10, as shown in FIG. 11A. Graft material 102 is attached to strut portions 12. Graft material 102 covers and is not attached to helical portions 14.

Figure 11B:
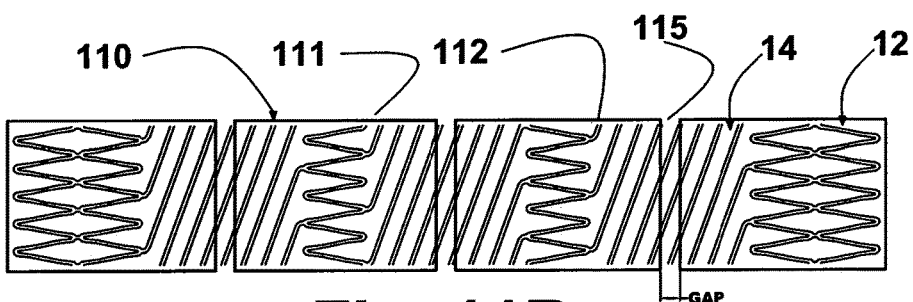
FIG. 11B is a side view of an alternate embodiment of a stent in accordance with the present invention including a plurality of sections of biocompatible graft material wherein a gap is provided between each of the sections of graft material.

Stent graft 110 comprises a plurality of sections 111 of graft material 112 covering the stent structure, as shown in FIG. 11B. Graft material 112 is attached to strut portions 12. Graft material 112 covers at least a portion of helical portions 14 and is not attached to helical portions 14. Gap 115 is positioned between adjacent sections 111 of graft material 112. Gap 115 will typically range in size between 0 (meaning no gap) and about 20% of the length of helical portion 14.

Figure 11C:
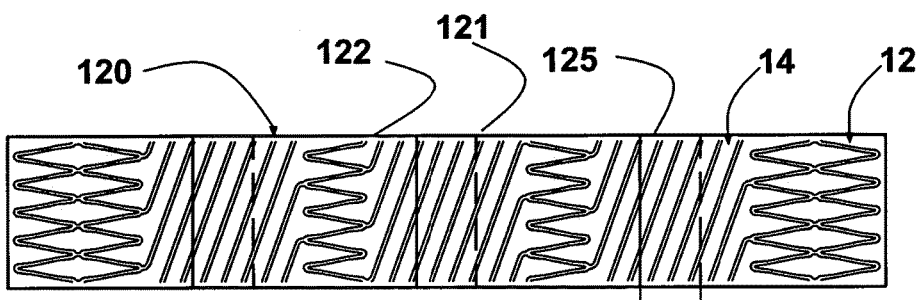
FIG. 11C is a side view of an alternate embodiment of a stent in accordance with the present invention including a plurality of sections of a biocompatible graft material wherein the graft material of adjacent sections is overlapped.

Stent graft 120 comprises a plurality of sections 121 of graft material 122 covering the stent structure, as shown in FIG. 11C. Graft material 122 is attached to strut portions 12. Graft material 122 covers and is not attached to helical portions 14. Sections 121 of graft material 122 are positioned such that there is an overlap 125 between adjacent sections 121 of graft material 122. Overlap 125 will typically range in size between 0 (meaning no gap) and about 40% of the length of helical portion 14.

Figure 11D:
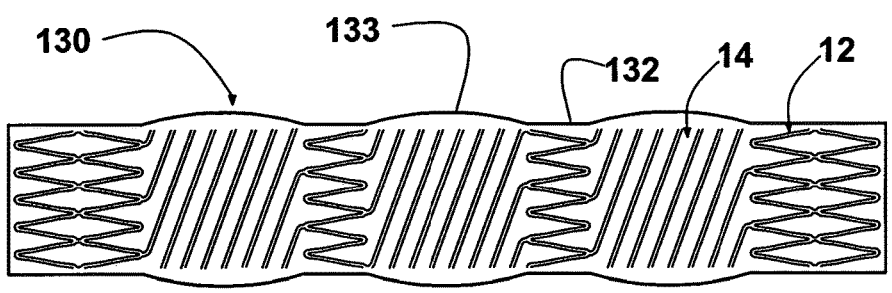
FIG. 11D is a side view of an alternate embodiment of a stent in accordance with the present invention including a biocompatible graft material, the graft material having a bulge at the helical portions.

Stent graft 130 comprises a continuous covering of graft material 132, as shown in FIG. 11D. Graft material 132 is attached to strut portions 12. Graft material 132 covers and is not attached to helical portions 14. Graft material 132 has bulge 133 at helical portions 14.

Figure 11E:
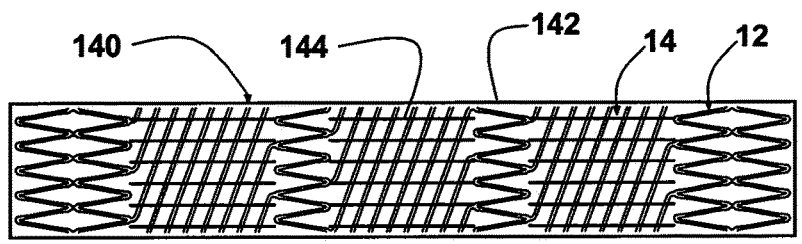
FIG. 11E is a side view of an alternate embodiment of a stent in accordance with the present invention including a biocompatible graft material, the graft material having a plurality of longitudinal openings over the helical portions.

Stent graft 140 comprises a continuous covering of graft material 142, as shown in FIG. 11E. Graft material 142 has a plurality of longitudinal openings 144 over helical portions 14.

Figure 11F:
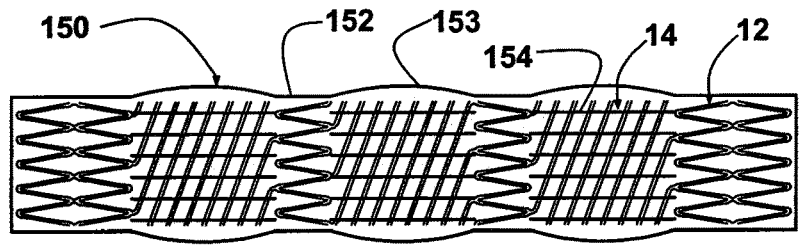
FIG. 11F is a side view of an alternate embodiment of a stent in accordance with the present invention the graft material having a bulge at the helical portions and the graft material having a plurality of longitudinal openings over the helical portions.
Figure 11G:
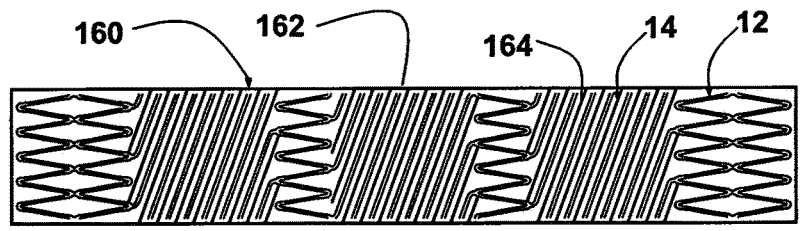
FIG. 11G is a side view of an alternate embodiment of a stent in accordance with the present invention including a biocompatible graft material having a plurality of helical openings corresponding to a pitch of the helical elements.

Stent graft 150 comprises a continuous covering of graft material 152, as shown in FIG. 11F. Graft material 152 has bulge 153 at helical portions 14 and has a plurality of longitudinal openings 154 over helical portions 14.

Stent graft 160 comprises a continuous covering of graft material 162, as shown in FIG. 11F. Graft material 162 has helical openings 164 in helical portions 14 that correspond to the pitch and angle of helical portions 14.

Figure 11H:
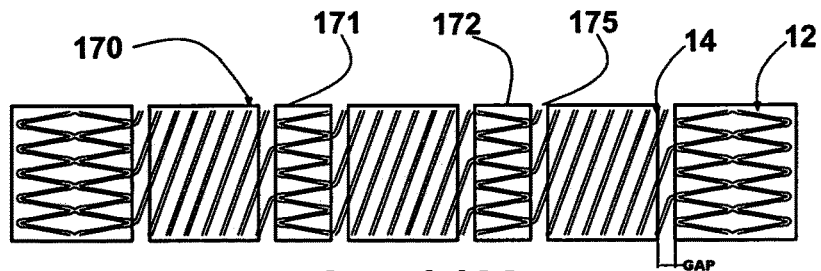
FIG. 11H is a side view of an alternate embodiment of a stent in accordance with the present invention including a plurality of sections of biocompatible graft material each of the sections being attached to either the strut portion or the helical portion wherein a gap is provided between each of the sections of graft material.

Stent graft 170 comprises a plurality of sections 171 of graft material 172 covering stent 10, as shown in FIG. 11H. Sections 171 can be attached to strut portions 12 or helical portions 14. Gap 175 is positioned between adjacent sections 171 of graft material 172. Gap 175 will typically range in size between 0 (meaning no gap) and about 20% of the length of helical portion 14.

Figure 11J:
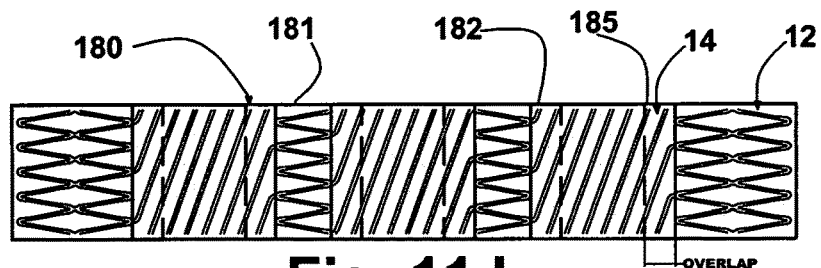
FIG. 11J is a side view of an alternate embodiment of a stent in accordance with the present invention including a plurality of sections of biocompatible graft material, each of the sections being attached to either the strut portion or the helical portion wherein adjacent sections of graft material is overlapped.

Stent graft 180 comprises a plurality of sections 181 of graft material 182 covering stent 10, as shown in FIG. 11J. Sections 181 can be attached to strut portions 12 or helical portions 14. Sections 181 of graft material 182 are positioned such that there is an overlap 185 between adjacent sections 181 of graft material 182. Overlap 185 will typically range in size between 0 (meaning no gap) and about 40% of the length of helical portion 14.

FIGS. 12A, 12B and 12C are plan views of stent 200 in accordance with the present invention. FIG. 12A shows stent 200 in an expanded state with gap 202 between helical elements 18. FIGS. 12B and 12C show stent 200 in two different compressed states. In FIG. 12B stent 200 is compressed such that gap 212 between side-by-side helical elements 18 is about the same throughout helical portion 14. The size of gap 212 between side-by-side helical elements 18 can range between 0 and about the size of the gap 202 in the expanded state, for example, as shown in FIG. 12A. In other words, when the size of the gap is 0, there is no space between side-by-side helical elements 18 and side-by-side helical elements 18 contact one another.

The helical elements of the stent shown in FIG. 12B have been wrapped around the stent a number of times such that in the crimped state the overall length 211 of the stent in the crimped state is the same as the overall length 201 of the stent in the expanded state shown in FIG. 12A, thereby eliminating foreshortening.

In FIG. 12C stent 200 is compressed such that helical element 18 is elongated and gap 222 between side-by-side helical elements 18 varies throughout the axial length of helical portion 14. The size of gap 222 between adjacent helical elements 18 can range between 0 and about the size of the gap 202 in the expanded state, for example, as shown in FIG. 12A. In other words, when the size of the gap is 0, there is no space between side-by-side helical elements 18 and side-by-side helical elements 18 contact one another. In FIG. 12C, the overall length 221 of the stent in the crimped state is greater then the overall length 201 of the stent in the expanded state.

An additional method can be provided to crimp the stent such that the length of helical portions is shorter in the crimped state than in the expanded state. For example, if the stent of FIG. 12A were crimped similar to that shown in FIG. 12B, except no gap exists between side-by-side helical elements the stent would be have length 211 in the crimped state which is shorter than length 201 in the expanded state. In one embodiment, a method of crimping provides a stent where the overall length is the same in the crimped and expanded state and there is no gap between helical elements in the crimped state.

As described above, one preferred embodiment of the stent is to permit repeated axial compression or expansion of about 20% and simultaneously permit bending with a minimum bending radius of about 13 mm. One method to construct a stent of the present invention with a specific target for flexibility is to vary the ratio between the sum of the gap space in the helical portion to the overall length. By increasing that ratio, the flexibility of the stent increases. This ratio will also be approximately the maximum axial compression the stent will allow. It will be appreciated that the maximum axial compression for safety may be limited by other factors such as strain in the helical elements.

Figure 13:
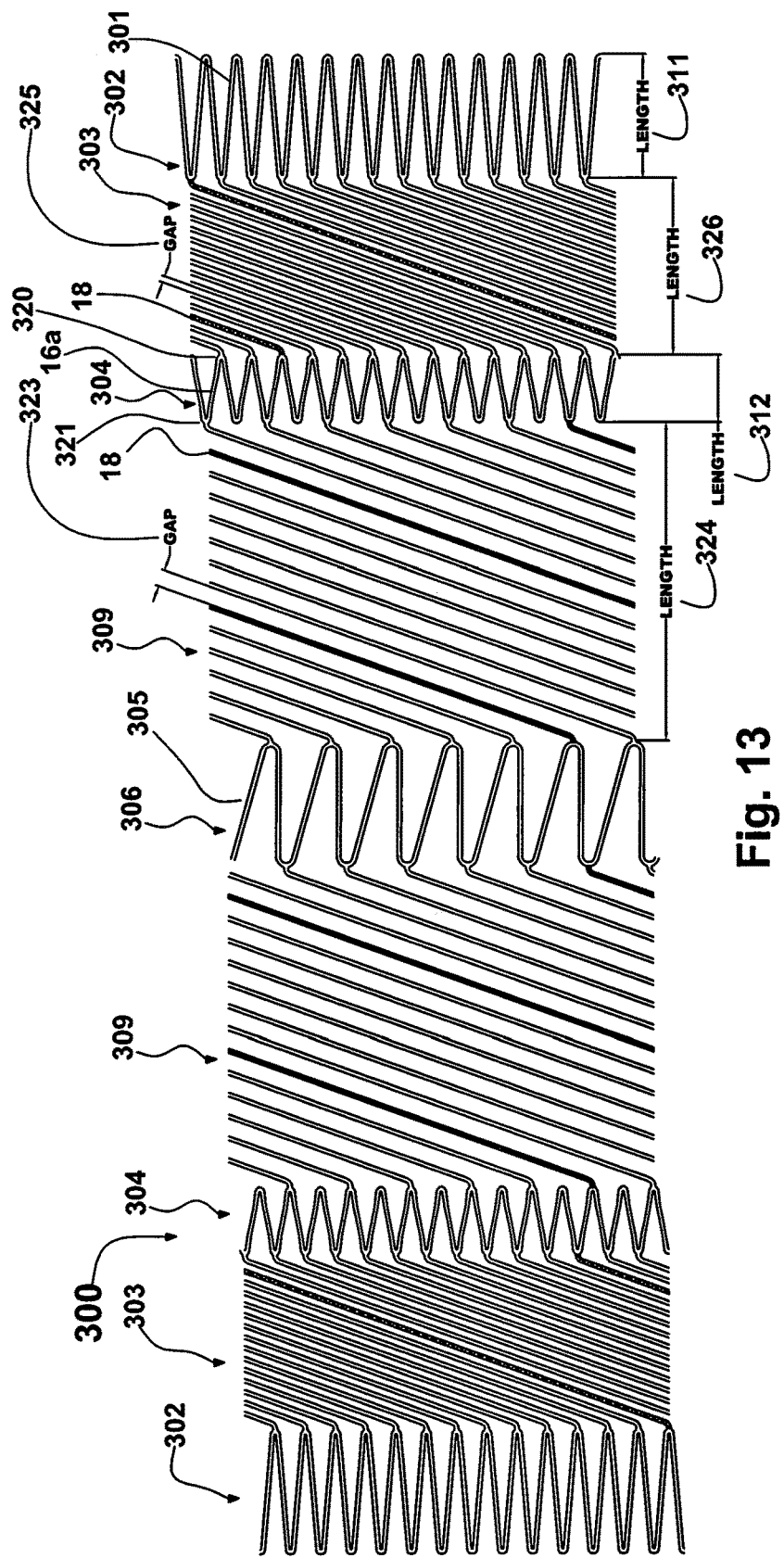
FIG. 13 is a plan view of an alternate embodiment of a stent in accordance with the present invention.

FIG. 13 is a plan view of a stent 300 in accordance with the present invention. Stent 300 is similar to other embodiments described above except it includes various configurations and various axial lengths of strut portions and various configurations and various axial lengths of helical portions. Strut portions 302 positioned at the outer most portion of stent 300 includes long strut elements 301. Long strut elements 301 have length 311. Length 311 of long strut element 301 is greater than length 312 of strut portions 304 positioned at the inner portion of stent 300. Long strut elements 301 provided on the ends of the stent may be advantageous to provide better anchoring and provide an area for adjacent stents to overlap, but not impede the flexibility of the helical portion. In some vasculatures, notably the femoropopliteal arteries, the length of diseased artery may be long, often longer than 10 cm. Multiple stents may be required to treat these long sections of diseased arteries. A common procedure in this case is to overlap the adjacent stents so that the vessel being treated is covered. When some conventional stents are overlapped in this manner, the mechanism which makes them flexible is impeded and this artificial stiffening can cause many problems, including stent fractures. An advantage of the present invention is that the elements that allow bending and axial flexibility (helical portion) are different than the elements that provide radial structure (strut portion) so that the strut portions on adjacent stents may overlap and not impede the movement of the helical portion and therefore the overall flexibility of the stent.

Helical portion 303 that is adjacent to the strut portion 302 comprises helical elements 18 that are connected to every strut element 301 of strut portion 302. Helical portion 303 can provide a high percentage of surface area for optimized delivery of a drug or other therapeutic agent. Strut portion 304 is connected to helical portion 303 by helical element 18 at every strut element 16a on side 320 of strut portion 304 and is connected to helical portion 309 at every other strut element 16a on side 321 of strut portion 304. Helical portion 309 provides a lower percentage of surface area and greater flexibility than helical portion 303. This type of configuration can provide a transition from a stiffer helical portion that has a high percentage of surface area to a more flexible helical portion.

Helical portion 309 has a higher ratio of the sum of gap lengths 323 to length 324 of helical portion 309 than the sum of gap lengths 325 to length 326 of helical portion 303, so that helical portion 309 will generally have greater flexibility.

Strut portion 306 has half as many strut elements 305 as strut portions 302 or 304 and therefore generally has more open area compared to strut portion 302 or strut portion 304. An advantage of a stent including a portion having a larger open area than other portions of the stent is that the larger open portion of the stent can be placed over an arterial bifurcation and not impede blood flow. Whereas the strut portion with a higher strut element density may impede blood flow.

The stent structure of the present invention, namely flexible helical portions flanked on either side by strut portions, provide an optimized structure where the strut portions stabilize a naturally unstable helical structure, and the helical portions provide net flexibility. There is substantial design optimization potential in combining various embodiments of the two portions.

The flexible stents and stent grafts of the present invention may be placed within vessels using procedures well known in the art. The flexible stents and stent grafts may be loaded into the proximal end of a catheter and advanced through the catheter and released at the desired site. Alternatively, the flexible stents and stent grafts may be carried about the distal end of the catheter in a compressed state and released at the desired site. The flexible stents or stent grafts may either be self-expanding or expanded by means such as an inflatable balloon segment of the catheter. After the stent(s) or stent graft(s) have been deposited at the desired intralumenal site, the catheter is withdrawn.

The flexible stents and stent grafts of the present invention may be placed within body lumen such as vascular vessels or ducts of any mammal species including humans, without damaging the lumenal wall. For example, the flexible stent can be placed within a lesion or an aneurysm for treating the aneurysm. In one embodiment, the flexible stent is placed in a super femoral artery upon insertion into the vessel, the flexible stent or stent grafts provides coverage of at least about 50% of the vessel.

Although presently preferred embodiments of the present invention have been disclosed for illustrative purposes, those skilled in the art will appreciate that many additions, modifications, and substitutions are possible without departing from the scope and spirit of the invention as defined by the accompanying claims. For example, a stent could be made with only right-handed or only left-handed helical portions, or the helical portions could have multiple reversals in winding direction rather than just one. Also, the helical portions could have any number of turns per unit length or a variable pitch, and the strut rings and/or helical portions could be of unequal length along the stent.

What is claimed is:

1. A flexible stent comprising: a helical portion comprising a plurality of side-by-side, individual helical elements helically wound about an axis of said stent, said helical portion being expandable radially upon deployment and compressible, expandable and bendable in a deployed state; and a strut portion on either side of said helical portion, each of said strut portions comprising axially aligned strut elements having a first end connected to said helical elements of said helical portion, said strut portions being radially expandable upon deployment, further comprising one or more additional said helical portions and one or more additional said strut portions wherein one of said one or more additional said helical portions is connected to a second end of one of said strut portions, said one or more additional said helical portions being connected respectively to said one or more additional said strut portions such that each of said helical portions is interposed between a pair of said strut portions, wherein said strut portions and/or said helical portions can have a varied axial length over a length of said stent;

wherein said strut elements of said strut portion have a wave pattern of individual wave portions, each individual wave portion having a peak and each of said helical elements is connected to a respective one of said peaks on one side of said side strut elements and some of said helical elements are connected to some of said peaks on the other side of said side strut elements, and every other one of said peaks of said strut elements are connected by a respective one of said helical elements;

wherein one of said helical portions has a higher ratio of a sum of gap lengths to a length of the helical portion than a second one of said helical portions; and wherein one of said strut portions has less strut elements than a second of said strut portions, said one of said strut portions has half as many strut elements as the second of said strut portions.

2. The stent of claim 1 wherein said helical elements of each of said helical portions are wound in the same direction.

3. The stent of claim 1 wherein at least one of said strut portions comprises a plurality of said strut elements, said strut elements of said strut portion have a wave pattern of individual wave portions, each individual wave portion having a peak and peaks of said individual wave members being connected to one another by a link.

4. The stent of claim 3 wherein said at least of said one strut portions is at either end of said stent.

5. The stent of claim 1 wherein at least one of said helical portions has a larger diameter than at least one of said strut portions.

* * * * *